(12) United States Patent
Chanduszko et al.

(10) Patent No.: US 7,691,112 B2
(45) Date of Patent: Apr. 6, 2010

(54) DEVICES, SYSTEMS, AND METHODS FOR SUTURING TISSUE

(75) Inventors: Andrzej Chanduszko, Weymouth, MA (US); Carol A. Devellian, Topsfield, MA (US); David R. Widomski, Wakefield, MA (US)

(73) Assignee: NMT Medical, Inc., Boston, MA (US)

( * ) Notice: Subject to any disclaimer, the term of this patent is extended or adjusted under 35 U.S.C. 154(b) by 746 days.

(21) Appl. No.: 10/833,725

(22) Filed: Apr. 27, 2004

(65) Prior Publication Data

US 2005/0059984 A1 Mar. 17, 2005

Related U.S. Application Data

(60) Provisional application No. 60/501,948, filed on Sep. 11, 2003.

(51) Int. Cl.
*A61B 17/10* (2006.01)
*A61B 17/08* (2006.01)

(52) U.S. Cl. .................. 606/139; 606/151

(58) Field of Classification Search .......... 606/108, 606/139, 142, 144, 148, 151, 213, 215, 219, 606/232; 227/67, 68; 128/898; 24/16 PB
See application file for complete search history.

(56) References Cited

U.S. PATENT DOCUMENTS

| | | |
|---|---|---|
| 3,077,733 A | 2/1963 | Axe et al. |
| 3,103,666 A | 9/1963 | Bone |
| 3,470,834 A | 10/1969 | Bone |
| 3,716,058 A | 2/1973 | Tanner, Jr. |
| 3,874,388 A | 4/1975 | King et al. |
| 3,875,648 A | 4/1975 | Bone |
| 3,990,619 A | 11/1976 | Russell |
| 4,006,747 A | 2/1977 | Kronenthal et al. |
| 4,007,743 A | 2/1977 | Blake |
| 4,039,078 A | 8/1977 | Bone |
| 4,235,238 A | 11/1980 | Ogiu et al. |
| 4,394,864 A | 7/1983 | Sandhaus |

(Continued)

FOREIGN PATENT DOCUMENTS

EP 553259 3/1995

(Continued)

OTHER PUBLICATIONS

Szili-Torok et al., Transseptal left heart catherisation guided by intracardiac echocardiography, Heart 2001, pp. 1-5.

(Continued)

*Primary Examiner*—Julian W Woo
(74) *Attorney, Agent, or Firm*—Finnegan, Henderson, Farabow, Garrett & Dunner, L.L.P.

(57) ABSTRACT

The invention relates to devices, systems, and methods for percutaneously suturing biological material, such as a patient's tissues. In one embodiment, a suturing device includes first and second tissue engaging members connected to one another by a first interconnecting member. In another embodiment, systems and methods are provided for forming holes through two overlapping layers of tissue. Subsequent to forming holes through the two layers of tissue, the suturing device is positioned through the holes to join or bring into contact the two layers of overlapping tissue.

15 Claims, 14 Drawing Sheets

U.S. PATENT DOCUMENTS

| | | | |
|---|---|---|---|
| 4,425,908 A | 1/1984 | Simon | |
| 4,485,816 A | 12/1984 | Krumme | |
| 4,515,583 A | 5/1985 | Sorich | |
| 4,556,050 A | 12/1985 | Hodgson | |
| 4,586,502 A * | 5/1986 | Bedi et al. | 606/144 |
| 4,669,473 A | 6/1987 | Richards et al. | |
| 4,696,300 A | 9/1987 | Anderson | |
| 4,705,040 A * | 11/1987 | Mueller et al. | 606/108 |
| 4,799,483 A | 1/1989 | Kraff | |
| 4,800,890 A | 1/1989 | Cramer | |
| 4,834,096 A | 5/1989 | Oh et al. | |
| 4,836,204 A | 6/1989 | Landymore et al. | |
| 4,844,066 A | 7/1989 | Stein | |
| 4,915,107 A | 4/1990 | Rebuffat et al. | |
| 4,985,014 A | 1/1991 | Orejola | |
| 5,021,059 A | 6/1991 | Kensey et al. | |
| 5,030,199 A | 7/1991 | Barwick et al. | |
| 5,037,433 A | 8/1991 | Wilk et al. | |
| 5,041,129 A | 8/1991 | Hayhurst et al. | |
| 5,042,976 A | 8/1991 | Ishitsu et al. | |
| 5,049,153 A | 9/1991 | Nakao et al. | |
| 5,057,114 A | 10/1991 | Wittich et al. | |
| 5,073,166 A | 12/1991 | Parks et al. | |
| 5,108,420 A | 4/1992 | Marks | |
| 5,112,310 A | 5/1992 | Grobe | |
| 5,171,259 A | 12/1992 | Inoue | |
| 5,190,528 A | 3/1993 | Fonger et al. | |
| 5,192,301 A | 3/1993 | Kamiya et al. | |
| 5,222,974 A | 6/1993 | Kensey et al. | |
| 5,236,440 A | 8/1993 | Hlavacek | |
| 5,257,637 A | 11/1993 | Gazayerli | |
| 5,282,827 A | 2/1994 | Kensey et al. | |
| 5,284,488 A | 2/1994 | Sideris | |
| 5,304,184 A | 4/1994 | Hathaway et al. | |
| 5,304,185 A | 4/1994 | Taylor | |
| 5,312,341 A | 5/1994 | Turi | |
| 5,312,435 A | 5/1994 | Nash et al. | |
| 5,320,633 A * | 6/1994 | Allen et al. | 606/144 |
| 5,334,217 A | 8/1994 | Das | |
| 5,336,252 A | 8/1994 | Cohen | |
| 5,354,308 A | 10/1994 | Simon et al. | |
| 5,357,979 A | 10/1994 | Imran | |
| 5,370,661 A | 12/1994 | Branch | |
| 5,403,338 A | 4/1995 | Milo | |
| 5,411,481 A | 5/1995 | Allen et al. | |
| 5,413,584 A | 5/1995 | Schulze | |
| 5,417,699 A | 5/1995 | Klein et al. | |
| 5,417,700 A | 5/1995 | Egan | |
| 5,425,744 A | 6/1995 | Fagan et al. | |
| 5,433,727 A | 7/1995 | Sideris | |
| 5,451,235 A | 9/1995 | Lock et al. | |
| 5,470,337 A * | 11/1995 | Moss | 606/139 |
| 5,478,353 A | 12/1995 | Yoon | |
| 5,486,185 A | 1/1996 | Freitas et al. | |
| 5,486,193 A | 1/1996 | Bourne et al. | |
| 5,507,811 A | 4/1996 | Koike et al. | |
| 5,540,712 A | 7/1996 | Kleshinski et al. | |
| 5,545,138 A | 8/1996 | Fugoso et al. | |
| 5,573,542 A | 11/1996 | Stevens | |
| 5,577,299 A | 11/1996 | Thompson et al. | |
| 5,578,045 A | 11/1996 | Das | |
| 5,597,378 A | 1/1997 | Jervis | |
| 5,601,571 A | 2/1997 | Moss | |
| 5,601,575 A | 2/1997 | Measamer et al. | |
| 5,618,311 A | 4/1997 | Gryskiewicz | |
| 5,620,461 A | 4/1997 | Muijs Van De Moer et al. | |
| 5,634,936 A | 6/1997 | Linden et al. | |
| 5,649,959 A | 7/1997 | Hannam et al. | |
| 5,683,411 A | 11/1997 | Kavteladze et al. | |
| 5,702,421 A | 12/1997 | Schneidt | |
| 5,709,707 A | 1/1998 | Lock et al. | |
| 5,713,908 A | 2/1998 | Jameel et al. | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,746,765 A | 5/1998 | Kleshinski et al. | |
| 5,749,895 A | 5/1998 | Sawyer et al. | |
| 5,776,162 A | 7/1998 | Kleshinski et al. | |
| 5,797,960 A | 8/1998 | Stevens et al. | |
| 5,800,516 A | 9/1998 | Fine et al. | |
| 5,810,848 A | 9/1998 | Hayhurst | |
| 5,810,884 A | 9/1998 | Kim | |
| 5,823,956 A | 10/1998 | Roth et al. | |
| 5,827,216 A | 10/1998 | Igo et al. | |
| 5,829,447 A | 11/1998 | Stevens et al. | |
| 5,836,311 A | 11/1998 | Borst et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,868,753 A | 2/1999 | Schatz | |
| 5,879,366 A | 3/1999 | Shaw et al. | |
| 5,885,238 A | 3/1999 | Stevens et al. | |
| 5,893,856 A | 4/1999 | Jacob et al. | |
| 5,895,404 A | 4/1999 | Ruiz | |
| 5,902,317 A | 5/1999 | Kleshinski et al. | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,927,284 A | 7/1999 | Borst et al. | |
| 5,928,250 A | 7/1999 | Koike et al. | |
| 5,944,738 A | 8/1999 | Amplatz et al. | |
| 5,964,782 A | 10/1999 | Lafontaine et al. | |
| 5,976,174 A | 11/1999 | Ruiz | |
| 5,989,268 A | 11/1999 | Pugsley, Jr. et al. | |
| 5,993,475 A | 11/1999 | Lin et al. | |
| 5,997,556 A | 12/1999 | Tanner | |
| 5,997,562 A | 12/1999 | Zadno-Azizi et al. | |
| 6,001,085 A | 12/1999 | Lurie et al. | |
| 6,007,558 A | 12/1999 | Ravenscroft et al. | |
| 6,010,517 A | 1/2000 | Baccaro | |
| 6,015,378 A | 1/2000 | Borst et al. | |
| 6,024,756 A | 2/2000 | Huebsch et al. | |
| 6,030,007 A | 2/2000 | Bassily et al. | |
| 6,030,405 A | 2/2000 | Zarbatany et al. | |
| 6,056,760 A | 5/2000 | Koike et al. | |
| 6,077,291 A | 6/2000 | Das | |
| 6,079,414 A | 6/2000 | Roth | |
| 6,080,182 A | 6/2000 | Shaw et al. | |
| 6,086,610 A | 7/2000 | Duerig et al. | |
| 6,113,609 A | 9/2000 | Adams | |
| 6,117,159 A | 9/2000 | Huebsch et al. | |
| 6,129,755 A | 10/2000 | Mathis et al. | |
| 6,132,438 A | 10/2000 | Fleischman et al. | |
| 6,142,975 A | 11/2000 | Jalisi et al. | |
| 6,149,664 A | 11/2000 | Kurz | |
| 6,152,918 A | 11/2000 | Padilla et al. | |
| 6,162,202 A | 12/2000 | Sicurelli et al. | |
| 6,165,183 A | 12/2000 | Kuehn et al. | |
| 6,165,204 A | 12/2000 | Levinson et al. | |
| 6,171,329 B1 | 1/2001 | Shaw et al. | |
| 6,174,322 B1 | 1/2001 | Schneidt | |
| 6,200,313 B1 | 3/2001 | Abe et al. | |
| 6,206,895 B1 | 3/2001 | Levinson | |
| 6,206,907 B1 | 3/2001 | Marino et al. | |
| 6,206,921 B1 | 3/2001 | Guagliano et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,228,097 B1 | 5/2001 | Levinson et al. | |
| 6,231,561 B1 | 5/2001 | Frazier et al. | |
| 6,245,080 B1 | 6/2001 | Levinson | |

| | | |
|---|---|---|
| 6,254,550 B1 | 7/2001 | McNamara et al. |
| 6,258,026 B1 | 7/2001 | Ravenscroft et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,278,371 B1 | 8/2001 | Hopkins |
| 6,290,674 B1 | 9/2001 | Roue et al. |
| 6,302,903 B1 | 10/2001 | Mulier et al. |
| 6,306,150 B1 | 10/2001 | Levinson |
| 6,312,446 B1 | 11/2001 | Huebsch et al. |
| 6,319,263 B1 | 11/2001 | Levinson |
| 6,322,548 B1 | 11/2001 | Payne et al. |
| 6,325,807 B1 | 12/2001 | Que |
| 6,328,688 B1 | 12/2001 | Borst et al. |
| 6,332,877 B1 | 12/2001 | Michels |
| 6,334,843 B1 | 1/2002 | Borst et al. |
| 6,336,898 B1 | 1/2002 | Borst et al. |
| 6,342,064 B1 | 1/2002 | Koike et al. |
| 6,344,049 B1 | 2/2002 | Levinson et al. |
| 6,346,074 B1 | 2/2002 | Roth |
| 6,348,041 B1 | 2/2002 | Klint |
| 6,348,059 B1 | 2/2002 | Hathaway et al. |
| 6,350,229 B1 | 2/2002 | Borst et al. |
| 6,352,531 B1 | 3/2002 | O'Connor et al. |
| 6,352,552 B1 | 3/2002 | Levinson et al. |
| 6,355,052 B1 | 3/2002 | Neuss et al. |
| 6,364,826 B1 | 4/2002 | Borst et al. |
| 6,364,846 B1 | 4/2002 | Nakamura |
| 6,364,853 B1 | 4/2002 | French et al. |
| 6,364,876 B1 | 4/2002 | Erb et al. |
| 6,371,906 B1 | 4/2002 | Borst et al. |
| 6,371,971 B1 | 4/2002 | Tsugita et al. |
| 6,375,625 B1 | 4/2002 | French et al. |
| 6,375,635 B1 | 4/2002 | Moutafis et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,394,948 B1 | 5/2002 | Borst et al. |
| 6,398,796 B2 | 6/2002 | Levinson |
| 6,402,772 B1 | 6/2002 | Amplatz et al. |
| 6,440,152 B1 | 8/2002 | Gainor et al. |
| 6,458,100 B2 | 10/2002 | Roue et al. |
| 6,460,749 B1 | 10/2002 | Levinson et al. |
| 6,464,629 B1 | 10/2002 | Boone et al. |
| 6,464,630 B1 | 10/2002 | Borst et al. |
| 6,482,210 B1 | 11/2002 | Skiba et al. |
| 6,482,224 B1 | 11/2002 | Michler et al. |
| 6,488,706 B1 | 12/2002 | Solymar |
| 6,494,888 B1 | 12/2002 | Laufer et al. |
| 6,527,786 B1 | 3/2003 | Davis et al. |
| 6,537,198 B1 | 3/2003 | Vidlund et al. |
| 6,544,274 B2 | 4/2003 | Danitz et al. |
| 6,551,344 B2 | 4/2003 | Thill |
| 6,572,593 B1 | 6/2003 | Daum |
| 6,596,013 B2 | 7/2003 | Yang et al. |
| 6,606,513 B2 | 8/2003 | Lardo et al. |
| 6,623,508 B2 | 9/2003 | Shaw et al. |
| 6,623,518 B2 | 9/2003 | Thompson et al. |
| RE38,335 E | 11/2003 | Aust et al. |
| 6,650,923 B1 | 11/2003 | Lesh et al. |
| 6,652,486 B2 | 11/2003 | Bialecki et al. |
| 6,663,592 B2 | 12/2003 | Rhad et al. |
| 6,685,724 B1 | 2/2004 | Haluck |
| 6,692,471 B2 | 2/2004 | Boudreaux |
| 6,702,835 B2 | 3/2004 | Ginn |
| 6,712,804 B2 | 3/2004 | Roue et al. |
| 6,712,836 B1 | 3/2004 | Berg et al. |
| 6,730,062 B2 | 5/2004 | Hoffman et al. |
| 6,730,081 B1 | 5/2004 | Desai |
| 6,855,124 B1 | 2/2005 | Gonzalez et al. |
| 6,939,348 B2 | 9/2005 | Malecki et al. |
| 7,220,265 B2 * | 5/2007 | Chanduszko et al. ........ 606/139 |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0044639 A1 | 11/2001 | Levinson |
| 2001/0049492 A1 | 12/2001 | Frazier et al. |
| 2002/0002373 A1 | 1/2002 | Boehlke et al. |
| 2002/0010481 A1 | 1/2002 | Jayaraman |
| 2002/0019648 A1 | 2/2002 | Akerfeldt et al. |
| 2002/0026094 A1 | 2/2002 | Roth |
| 2002/0026208 A1 | 2/2002 | Roe et al. |
| 2002/0029048 A1 | 3/2002 | Miller |
| 2002/0032462 A1 | 3/2002 | Houser et al. |
| 2002/0043307 A1 | 4/2002 | Ishida et al. |
| 2002/0045908 A1 | 4/2002 | Nobles et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0167055 A1 | 9/2003 | Kolata et al. |
| 2003/0181937 A1 | 9/2003 | Osterlind |
| 2003/0191494 A1 | 10/2003 | Gray et al. |
| 2003/0195530 A1 | 10/2003 | Thill |
| 2003/0195531 A1 | 10/2003 | Gardiner et al. |
| 2003/0208232 A1 | 11/2003 | Blaeser et al. |
| 2003/0212435 A1 | 11/2003 | Gold et al. |
| 2004/0138701 A1 | 7/2004 | Haluck |
| 2004/0193147 A1 | 9/2004 | Malecki et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2005/0021016 A1 | 1/2005 | Malecki et al. |
| 2005/0034735 A1 | 2/2005 | Deem et al. |
| 2005/0080406 A1 | 4/2005 | Malecki et al. |
| 2005/0101984 A1 | 5/2005 | Chanduszko et al. |
| 2005/0131401 A1 | 6/2005 | Malecki et al. |
| 2005/0131460 A1 | 6/2005 | Gifford, III et al. |
| 2006/0027241 A1 | 2/2006 | Malecki et al. |
| 2006/0074410 A1 | 4/2006 | Malecki et al. |

FOREIGN PATENT DOCUMENTS

| | | |
|---|---|---|
| EP | 1 013 227 A2 | 6/2000 |
| EP | 1 046 375 A1 | 10/2000 |
| EP | 724406 | 12/2001 |
| EP | 1222897 | 7/2002 |
| WO | WO 9206733 | 4/1992 |
| WO | WO 9510983 | 4/1995 |
| WO | WO 95/13111 | 5/1995 |
| WO | WO 9807375 | 2/1998 |
| WO | WO 9918862 | 4/1999 |
| WO | WO 9918864 | 4/1999 |
| WO | WO 9918870 | 4/1999 |
| WO | WO 9918871 | 4/1999 |
| WO | WO 99/25254 | 5/1999 |
| WO | WO 00/27292 | 5/2000 |
| WO | WO 01/49185 | 7/2001 |
| WO | WO 01/78596 | 10/2001 |
| WO | WO 0241790 | 5/2002 |

| WO | WO 03022159 | 3/2003 |
| WO | WO 03/059152 | 7/2003 |
| WO | WO 03077733 | 9/2003 |
| WO | WO 03088818 | 12/2003 |
| WO | WO 2004/028348 | 4/2004 |

OTHER PUBLICATIONS

International Searching Aurhority, "Communication Relating to the Results of the Partial International Search," PCT Application No. PCT/US2004/012913, mailed on Sep. 29, 2004, 2 pgs.

International Search Report (PCT Rule 44.1); International Application No. PCT/US2004/012913; mailed on Feb. 24, 2005; 11 pgs.

Written Opinion (PCT Rule 43bis. 1); International Application No. PCT/US2004/12913; mailed on Feb. 24, 2005; 7 pgs.

De Ponti, R. et al., "Trans-septal Catheterization for Radiofrequency Catheter Ablation of Cardiac Arrhythmias. Results and Safety of a Simplified Method," European Heart Journal, vol. 19, Jun. 1998, pp. 943-950.

"Elastic Deployment," SMST-2000 Proceedings of the International Conference on Shape Memory and Superelastic Technologies, Apr. 30 to May 4, 2000, Asilomar Conference Center, 3 pages.

Hansen J., "Metals that Remember," Science 81, June, pp. 44-47.

Kotan, C. et al., Diameter and Pressure of the Water-Jet for Liver Resection, Easter J. Med., 6(2):43-47. 2001.

Hawkins, Jr. I.F., M.D., et al., "The Puncture Needle as Guidewire: Needle Guide Technique for Percutaneous Nephrostomy," Seminars in Interventional Radiology, vol. 4, No. 2, Jun. 1987, pp. 126-130.

Protsenko, J.A., "Electrosurgical Tissue Resection: a Numerical and Experimental Study, Proceedings of SPIE," vol. 4954, pp. 64-70.

Nat'l Aeronautics and Space Administration, "55-Nitinol—The Alloy with a Memory: Its Physical Metallurgy, Properties, and Applications," A Report, pp. 24-25.

Kramer, P. M.D., "PFO and Stroke: The Hidden Connection," Endovascular Today, http://www.endovasculartoday.com/02_current/10.html, printed Oct. 9, 2003.

Kimura, A., et al., "Effects of Neutron Irradiation on the Transformation Behavior in Ti-Ni Alloys," Abstract, Proceedings of the Int'l Conf. On Mariensitic Transformations (1992) pp. 935-940.

Ramanathan, G., et al., "Experimental and Computational Methods for Shape Memory Alloys," $15^{th}$ ASCE Engineering Mechanics Conf, Jun. 2-5, 2003.

Ruiz, C.E. M.D., Ph.D., et al., "The Puncture Technique: A New Method of Transcatheter Closure of Patent Foramen Ovale," Catheterization and Cardiovascular Interventions, vol. 53, 2001, pp. 369-372.

Shabalovskaya, S., "Surface, corrosion and biocompatibility aspects of Nitinol as an implant material," Bio-Medical materials and Engineering, (2002) vol. 12, pp. 69-109.

Sommer, RJ M.D., et al., "New Transseptal Puncture Technique for Transcatheter Closure of Patent Foramen Ovale," Mount Sinai Medical Center, New York, New York, publication date unknown but believed to be Jun. 2002 or earlier.

Stöckel, "Nitinol Medical Devices and Implants," SMST-2000: Proceedings of the International Conference on Shape Memory and Suerelastic Technologies, pp. 531-541.

Uchil, J. "Shape Memory Alloys—Characterization Techniques," Pramana—Journal of Physics, (2002) vol. 58, Nos. 5 & 6, pp. 1131-1139.

* cited by examiner

DEVICES, SYSTEMS, AND METHODS FOR SUTURING TISSUE

CROSS-REFERENCE TO RELATED APPLICATION

This application incorporates by reference, and claims priority to and the benefit of, U.S. provisional application Ser. No. 60/501,948, which was filed on Sep. 11, 2003.

TECHNICAL FIELD

The invention generally relates to devices, systems, and methods for percutaneously suturing tissue. More particularly, the invention relates to a suturing device that includes at least two tissue engaging members connected to one another by an interconnecting member.

BACKGROUND

A septum is generally defined as a dividing muscular wall, membrane, or tissue between two or more bodily spaces. For example, the human heart is divided into four compartments or chambers. The left and right atria are located in the upper portion of the heart and the left and right ventricles are located in the lower portion of the heart. The left and right atria are separated from each other by the intraatrial septum, while the ventricles are separated by the intraventricular septum.

Septal defects can take various forms. An exemplary septal defect is a patent foramen ovale. The patent foramen ovale is a persistent, one-way, usually flap-like opening or tunnel in the wall between the right atrium and the left atrium of the heart. More specifically, the patent foramen ovale is formed by two layers of partially overlapping, but unfused, cardiac tissue (i.e., the septum primum and the septum secundum).

Under certain conditions, right atrial pressure exceeds left atrial pressure, creating the possibility for right to left shunting of blood through the patent foramen ovale. Blood clots may thereby enter the systemic circulation. This is particularly problematic for patients who are prone to forming venous thrombus, such as those with deep vein thrombosis or clotting abnormalities.

Improved devices, systems, and methods for suturing septal defects, such as, for example, patent foramen ovale, are needed.

SUMMARY OF THE INVENTION

The present invention relates to devices, systems, and methods for suturing together biological material, such as layers of tissue. In particular, in one embodiment, the present invention facilitates the percutaneous closure of a patent foramen ovale. According to an embodiment of the invention, the physician forms holes, for example, through the septum secundum and the septum primum in an area where the septa overlap. Subsequent to forming the holes, the physician positions the suturing device of the invention through the holes to bring into contact the two overlapping layers of tissue. Optionally, the physician also uses a tissue stabilization device to facilitate the procedure of closing the patent foramen ovale.

In general, in one aspect, the invention relates to a suturing system. The suturing system includes a suturing device, which itself includes first and second tissue engaging members and a first interconnecting member. The first tissue engaging member includes a first end, a second end, and a first intermediate portion positioned between the first end and the second end, while the second tissue engaging member includes a third end, a fourth end, and a second intermediate portion positioned between the third end and the fourth end. The first interconnecting member includes a first fixed end connected to the first intermediate portion of the first tissue engaging member, and a second fixed end connected to the second tissue engaging member. The suturing device is insertable into a patient in this connected configuration.

Various embodiments of this aspect of the invention include the following features. The second fixed end of the first interconnecting member may be connected to the second intermediate portion of the second tissue engaging member. The first and/or second tissue engaging members may be substantially cylindrical and they may have an atraumatic structure. For example, one or more ends of the first and/or second tissue engaging members may be rounded. In another embodiment, the first interconnecting member is made, either entirely or in part, from a resilient material. In one such embodiment, the first interconnecting member is reciprocally moveable between an unstressed position and a deformed position. In yet another embodiment, the first interconnecting member includes a stretchable material.

In still another embodiment, the tissue engaging members and/or the first interconnecting member include a material for stimulating tissue growth, such as, for example, collagen. Alternatively, the tissue engaging members and/or the first interconnecting member include a bioabsorbable material, such as, for example, a polylactic acid.

In one embodiment, the suturing device further includes a second interconnecting member connected to the first tissue engaging member and/or the second tissue engaging member. Moreover, the suturing device may further include a third tissue engaging member connected to the second interconnecting member, or, alternatively, to the first fixed end or the second fixed end of the first interconnecting member.

In a further embodiment, the suturing system also includes an elongate member. The elongate member includes a proximal end, a distal end, a wall extending from the proximal end to the distal end, and a cutting member positioned at the distal end. In one such embodiment, the wall of the elongate member defines a lumen that extends from the proximal end to the distal end of the elongate member, and the wall also defines an opening at the distal end of the elongate member. Moreover, the suturing device and a delivery member, which may be releasably connected to the suturing device, may be disposed within the lumen of the elongate member. Also, the elongate member may further include a retractable gate member positioned at the distal end of the elongate member. Alternatively, in another such embodiment, the first tissue engaging member includes a first lumen that extends from the first end to the second end of the first tissue engaging member, the second tissue engaging member includes a second lumen that extends from the third end to the fourth end of the second tissue engaging member, and the elongate member is disposed within the first lumen of the first tissue engaging member and also within the second lumen of the second tissue engaging member.

In another aspect, the invention provides another suturing device. The suturing device includes a first tissue engaging member, a second tissue engaging member, a first interconnecting member connecting the first tissue engaging member to the second tissue engaging member, and a first anchor connected to the first tissue engaging member.

In one embodiment of this aspect of the invention, the suturing device further includes a second anchor connected to the second tissue engaging member. One or both of the first anchor and the second anchor may be a spiral tissue anchor or a barbed tissue anchor.

In yet another aspect, the invention provides methods for suturing tissue. The methods include inserting one of the suturing devices described above into a heart of a patient and attaching the suturing device to one or more tissue surfaces in the heart of the patient.

In one embodiment of this aspect of the invention, the septum primum and the septum secundum are the tissue surfaces in the heart of the patient to which the suturing device is attached. In one such embodiment, the method for suturing tissue further includes positioning a tissue stabilization device in a patent foramen ovale.

In another embodiment, attaching the suturing device to the tissue surfaces in the heart of a patient includes extending the first tissue engaging member through a first hole in a first tissue layer and through a second hole in a second tissue layer, positioning the first tissue engaging member on a tissue surface of the second tissue layer, and positioning the second tissue engaging member on a tissue surface of the first tissue layer. Alternatively, in yet another embodiment, attaching the suturing device to the tissue surfaces in the heart of the patient includes extending the first tissue engaging member through a first hole in a first tissue layer, positioning the first tissue engaging member on a tissue surface of the first tissue layer, extending the second tissue engaging member through a second hole in a second tissue layer, and positioning the second tissue engaging member on a tissue surface of the second tissue layer.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed on illustrating the principles and concepts of the invention.

DESCRIPTION

The present invention relates to devices, systems, and methods for percutaneously suturing together biological material, such as layers of tissue. For example, in accordance with the invention, the septum primum and the septum secundum of a patent foramen ovale are sutured together.

Throughout the description, where devices are described as having, including, or comprising specific components, or where methods are described as having, including, or comprising specific method steps, it is contemplated that the devices of the present invention also consist essentially of, or consist of, the recited components, and that the methods of the present invention also consist essentially of, or consist of, the recited method steps.

In broad overview, a suturing device of the invention includes, in one embodiment, two tissue engaging members interconnected by an interconnecting member. In order to suture together two layers of tissue, the suturing device of the invention is, in one embodiment, placed through holes formed in the two layers of tissue. Each of the two tissue engaging members then engages one of the two layers of tissue. Optionally, a suturing system of the invention includes a cutting member for forming the holes in the layers of tissue.

Figure 1:
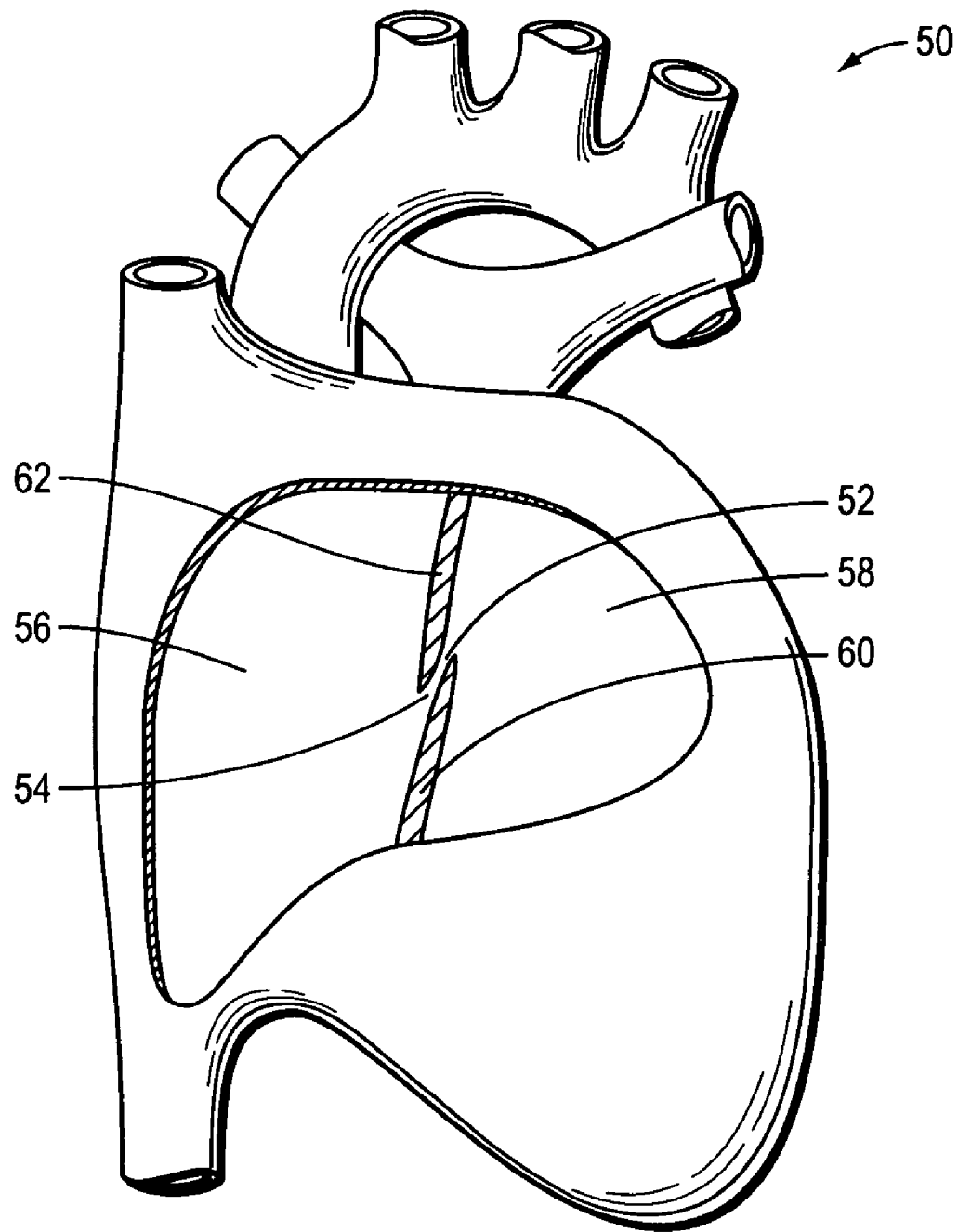
FIG. 1 is a cutaway view of a heart illustrating a patent foramen ovale.

FIG. 1 depicts a cutaway view of a heart 50, including an exemplary abnormal opening, a patent foramen ovale 52, that can be corrected by the devices, systems, and methods of the present invention. The view of the heart 50 depicted in FIG. 1 includes a septum 54 that divides a right atrium 56 from a left atrium 58. The septum 54 includes a septum primum 60 and a septum secundum 62. The patent foramen ovale 52 is located between the septum primum 60 and the septum secundum 62. The patent foramen ovale 52 provides an undesirable fluid communication between the right atrium 56 and the left atrium 58 and, under certain conditions, allows for the shunting of blood from the right atrium 56 to the left atrium 58. If the patent foramen ovale 52 is not closed or obstructed in some manner, a patient is placed at high risk for an embolic stroke.

Figure 2:
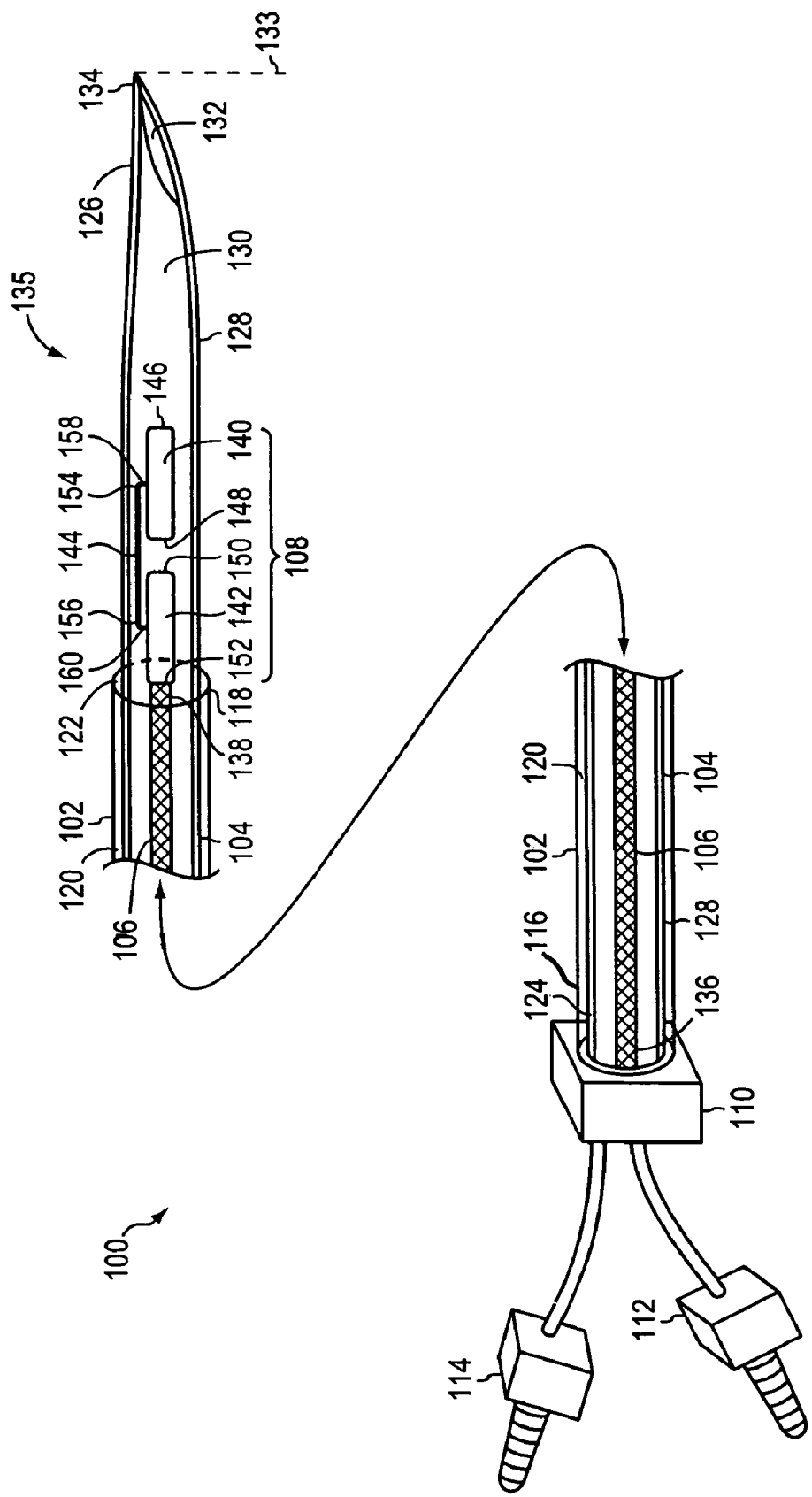
FIG. 2 is a schematic fragmented view of a tissue suturing system according to an illustrative embodiment of the invention.

FIG. 2 depicts a tissue suturing system 100 according to an illustrative embodiment of the invention. In one embodiment, the tissue suturing system 100 includes a sheath 102, an elongate member 104, a delivery member 106, a suturing device 108, an interface 110, a first controller 112, and a second controller 114.

In one embodiment, the sheath 102 includes a proximal end 116 (i.e., an end that is closest to a physician when the physician is operating the tissue suturing system 100) and an opposite, distal end 118. In one embodiment, the proximal end 116 of the sheath 102 is connected to the interface 110. In another embodiment, the sheath 102 defines a lumen 120 that extends from the proximal end 116 to the distal end 118 of the sheath 102, and an opening 122 located at the distal end 118 of the sheath 102. The opening 122 is in fluid communication with the lumen 120 of the sheath 102. In one embodiment, the sheath 102 is a transseptal sheath, such as, for example, item number RCF-10.0-38-80-J-RB Large Check-Flo® Blue Introducer Set, which is manufactured by Cook Incorporated of Bloomington, Ind.

With continued reference to FIG. 2, at least partially disposed within the lumen 120 of the sheath 102 is the elongate member 104. The elongate member 104 includes a proximal end 124, an opposite, distal end 126, and a wall 128 extending from the proximal end 124 to the distal end 126. In one embodiment, the wall 128 of the elongate member 104 defines a lumen 130 that extends from the proximal end 124 to the distal end 126 of the elongate member 104, and an opening 132 at the distal end 126 of the elongate member 104. In another embodiment, the elongate member 104 includes, at its distal end 126, a cutting member 134 that is used, for example, to create one or more holes through a patient's tissues. The cutting member 134 may be, for example, a sharp point or protrusion formed at the distal end 126 of the elongate member 104 by, for example, trimming the distal end 126 of the elongate member 104 at an angle from a line 133 drawn perpendicular to the long axis of the elongate member 104.

The elongate member 104 according to the invention can achieve an extended position and a retracted position. Referring to FIG. 2, in the extended position of the elongate member 104, a distal portion 135 of the elongate member 104 is positioned distal to the distal end 118 of the sheath 102. In the retracted position of the elongate member 104, the entire elongate member 104 is positioned proximal to the distal end 118 of the sheath 102, i.e., within the lumen 120 of the sheath 102 (not shown). The sheath 102 may thus enclose the cutting member 134 of the elongate member 104 while the physician inserts the tissue suturing system 100 into the heart of a patient.

In one embodiment, the elongate member 104 is reciprocally moved between the extended and retracted positions by slideable movement of the elongate member 104 within the lumen 120 of the sheath 102 along the longitudinal axis of the sheath 102. Alternatively, the elongate member 104 may be stationary and may be alternated between the extended position and the retracted position by proximally withdrawing the sheath 102 over the elongate member 104 to extend the elongate member 104, and by distally advancing the sheath 102 over the elongate member 104 to retract the elongate member 104.

Referring still to FIG. 2, in one embodiment, the delivery member 106 and the suturing device 108 are initially disposed within the lumen 130 of the elongate member 104. The exemplary delivery member 106 includes a proximal end 136 and an opposite, distal end 138. The distal end 138 of the delivery member 106 may be positioned adjacent the suturing device 108 to engageably contact the suturing device 108. In one embodiment, the distal end 138 of the delivery member 106 is releasably connected to the suturing device 108. For example, the distal end 138 of the delivery member 106 may include a mechanical claw (not shown) for grasping and releasing the suturing device 108. Alternatively, in another embodiment, the suturing device 108 includes an eyelet (not shown). In one such embodiment, thread (not shown) is connected to the delivery member 106 and is passed through the eyelet of the suturing device 108 to connect the delivery member 106 to the suturing device 108. Cutting the thread releases the suturing device 108 from the delivery member 106. A variety of other means may be used to releasably connect the distal end 138 of the delivery member 106 to the suturing device 108.

The delivery member 106 slideably moves within the lumen 130 of the elongate member 104. Accordingly, because the delivery member 106 may be positioned to abut and/or to engageably contact the suturing device 108, slideable movement of the delivery member 106 along a longitudinal axis of the elongate member 104 can result in a corresponding movement of the suturing device 108 along the longitudinal axis of the elongate member 104. In one embodiment, extending the delivery member 106 toward the distal end 126 of the elongate member 104 extends the suturing device 108 toward the distal end 126 of the elongate member 104 and distal to the opening 132 located at the distal end 126 of the elongate member 104.

Figure 3:
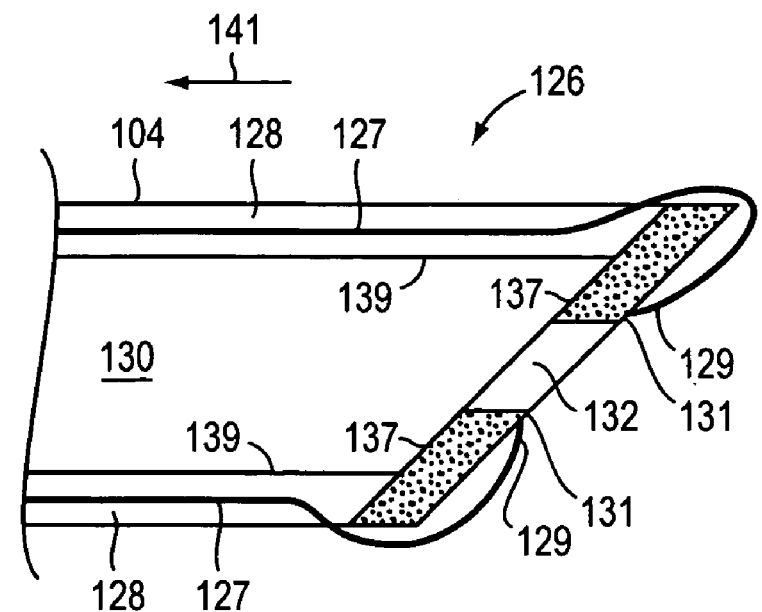
FIG. 3 is a schematic cross-sectional view of a distal end of an elongate member for a tissue suturing system, with a gate member of the elongate member in an extended position, according to an illustrative embodiment of the invention.
Figure 4:
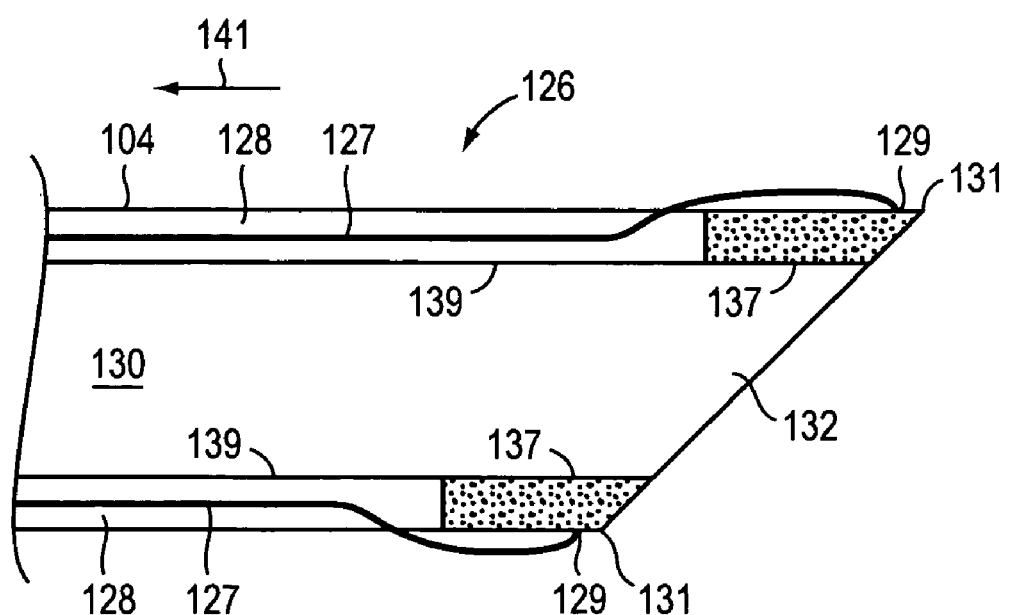
FIG. 4 is a schematic cross-sectional view of the distal end of the illustrative elongate member of FIG. 3 with the gate member of the elongate member in a retracted position.

FIGS. 3 and 4 depict a schematic cross-sectional view of the distal end 126 of the elongate member 104 according to illustrative embodiments of the invention. Optionally, as illustrated in FIGS. 3 and 4, the elongate member 104 can include a gate member 137. In one embodiment, the gate member 137 is positioned, as illustrated in FIGS. 3 and 4, at the distal end 126 of the elongate member 104. Alternatively, the gate member 137 may be positioned anywhere along the long axis of the elongate member 104.

In one embodiment, the gate member 137 is moveable between an extended position, illustrated in FIG. 3, and a retracted position, illustrated in FIG. 4. When placed in the extended position, the gate member 137 projects from an inner surface 139 of the wall 128 of the elongate member 104 into the lumen 130 of the elongate member 104, thereby preventing the suturing device 108 from being extended distal to the opening 132 located at the distal end 126 of the elongate member 104.

In one embodiment, the distal end 126 of the elongate member 104 is designed such that the gate member 137 achieves the extended position unless the physician acts to move the gate member 137 from the extended position by, for example, applying a force to or actuating the gate member 137. For example, the distal end 126 of the elongate member 104 may be made of a shape memory material designed to place the gate member 137 in its extended position absent any forces on, or actuation of, the gate member 137. In one such embodiment, one or more actuating strings 127 extend along a length of the elongate member 104 from the proximal end 124 of the elongate member 104 towards the distal end 126 of the elongate member 104. As illustrated in FIGS. 3 and 4, the one or more actuating strings 127 may be encapsulated within the wall 128 of the elongate member 104 and each one of the actuating string(s) 127 may connect at a distal end 129 of the actuating string(s) 127 to an end 131 of the gate member 137. Accordingly, with the gate member 137 in the extended position (FIG. 3), to place the gate member 137 in the retracted position (FIG. 4), the physician pulls on the actuating string(s) 127 in the direction of arrow 141 to rotate the gate member 137 away from the lumen 130 of the elongate member 104. When the physician releases the actuating string(s) 127, the shape memory material of the distal end 126 of the elongate member 104 returns the gate member 137 to the extended position.

Alternatively, in another embodiment, the gate member 137 requires actuation to be placed in the extended position. In one such embodiment, the physician places the gate member 137 in the extended position by, for example, rotating the entire, or one or more portions of the, wall 128 at the distal end 126 of the elongate member 104 towards the lumen 130 of the elongate member 104. For example, the physician employs a controller, as described below, to rotate the gate member 137 between the extended position and the retracted position.

In one embodiment, as illustrated in FIG. 3, the gate member 137, when placed in the extended position, continuously extends from and around the entire perimeter of the inner surface 139 of the elongate member 104. Alternatively, the gate member 137 may extend from a single portion of the perimeter of the inner surface 139, or the gate member 137 may intermittently extend from different portions of the perimeter of the inner surface 139 of the elongate member 104.

With reference to FIG. 4, when the gate member 137 is retracted to the retracted position, the gate member 137 no longer projects into the lumen 130 of the elongate member 104. Accordingly, with the gate member 137 placed in the retracted position, the suturing device 108 may be extended distal to the opening 132 located at the distal end 126 of the elongate member 104.

In one embodiment, the elongate member 104 and the delivery member 106 are flexible tubes fabricated from biocompatible materials, such as, for example, polyethylene, polyether-block amide copolymer (e.g., PEBAX®, which is manufactured by Atofina Chemicals of Philadelphia, Pa.), polyurethane, or fluorinated ethylene propylene. In another embodiment, the elongate member 104 and/or the delivery member 106 are made entirely from metal (e.g., stainless steel or Nitinol, which is a nickel-titanium alloy manufactured by Nitinol Devices and Components of Freemont, Calif.). In yet another embodiment, the elongate member 104 and/or the delivery member 106 have a polymer shaft with a metallic tip.

Referring again to FIG. 2, also illustrated is an exemplary interface 110 that permits, in some embodiments, the first controller 112 and the second controller 114 to communicate with the elongate member 104 and the delivery member 106, respectively. To enable such communication, the proximal end 124 of the elongate member 104 and the proximal end 136 of the delivery member 106 each connect to the interface 110. The exemplary first controller 112 and the exemplary second controller 114 may, for example, extend, retract, or otherwise manipulate the elongate member 104, including the gate member 137 of the elongate member 104, and the delivery member 106, respectively.

A single controller could, alternatively, control all functions and operations of the tissue suturing system 100 and the instruments disposed therein. Alternatively, a plurality of controllers (e.g., a distal end controller for extending and retracting the distal end of an instrument, a tip bending controller for altering the angular orientation of a portion of an instrument, and an extension controller for extending and retracting a component of an instrument) may be provided, each one controlling different components or functions of the tissue suturing system 100, as is known to one skilled in the art. For example, a separate gate member controller may be provided for extending, retracting, or otherwise manipulating the gate member 137 of the elongate member 104. In yet another embodiment, the physician operates the tissue suturing system 100 by extending, retracting, or otherwise manipulating the elongate member 104, the gate member 137 of the elongate member 104, and the delivery device 106 manually, without the use of any controllers.

Figure 5:
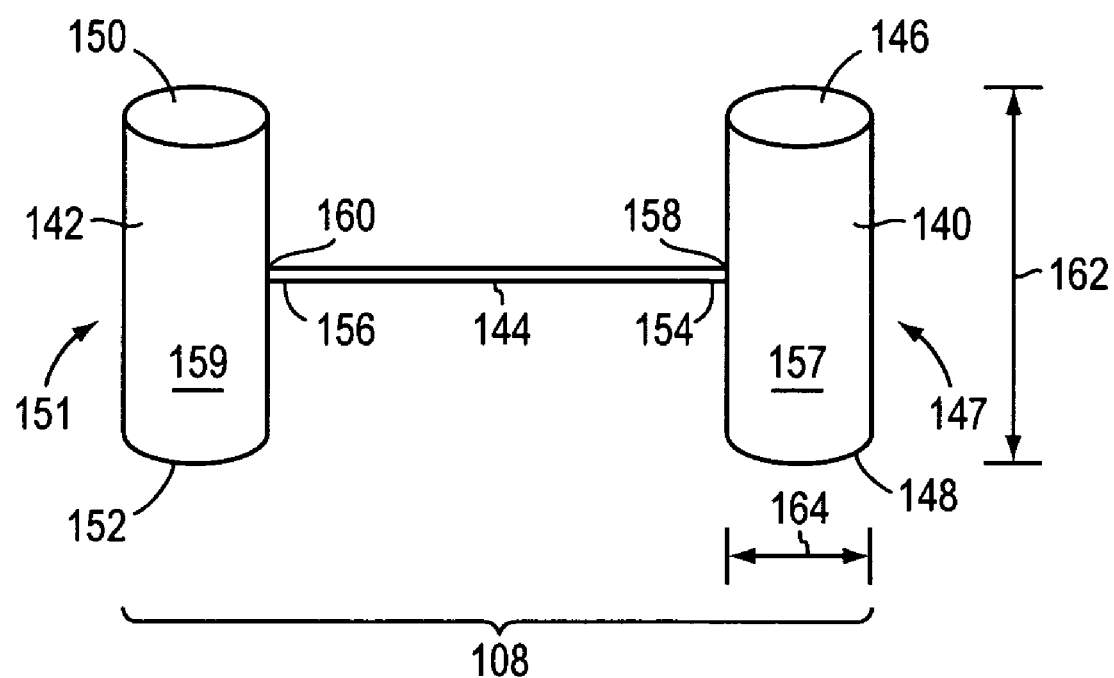
FIG. 5 is a schematic perspective view of a suturing device in a connected configuration according to an illustrative embodiment of the invention.

FIG. 5 depicts a suturing device 108 in a connected configuration according to an illustrative embodiment of the invention. Referring to FIGS. 2 and 5, the illustrative suturing device 108 includes a first tissue engaging member 140, a second tissue engaging member 142, and a first interconnecting member 144. In one embodiment, the first tissue engaging member 140 includes a first end 146, an opposite, second end 148, and an intermediate portion 147 that is positioned between the first end 146 and the second end 148. Similarly, the second tissue engaging member 142 includes a first end 150, a second end 152 that is opposite to the first end 150, and an intermediate portion 151 that is positioned between the first end 150 and the second end 152. For its part, the first interconnecting member 144 includes a first fixed end 154 that is connected to the first tissue engaging member 140, and an opposite, second fixed end 156 that is connected to the second tissue engaging member 142.

Figure 6:
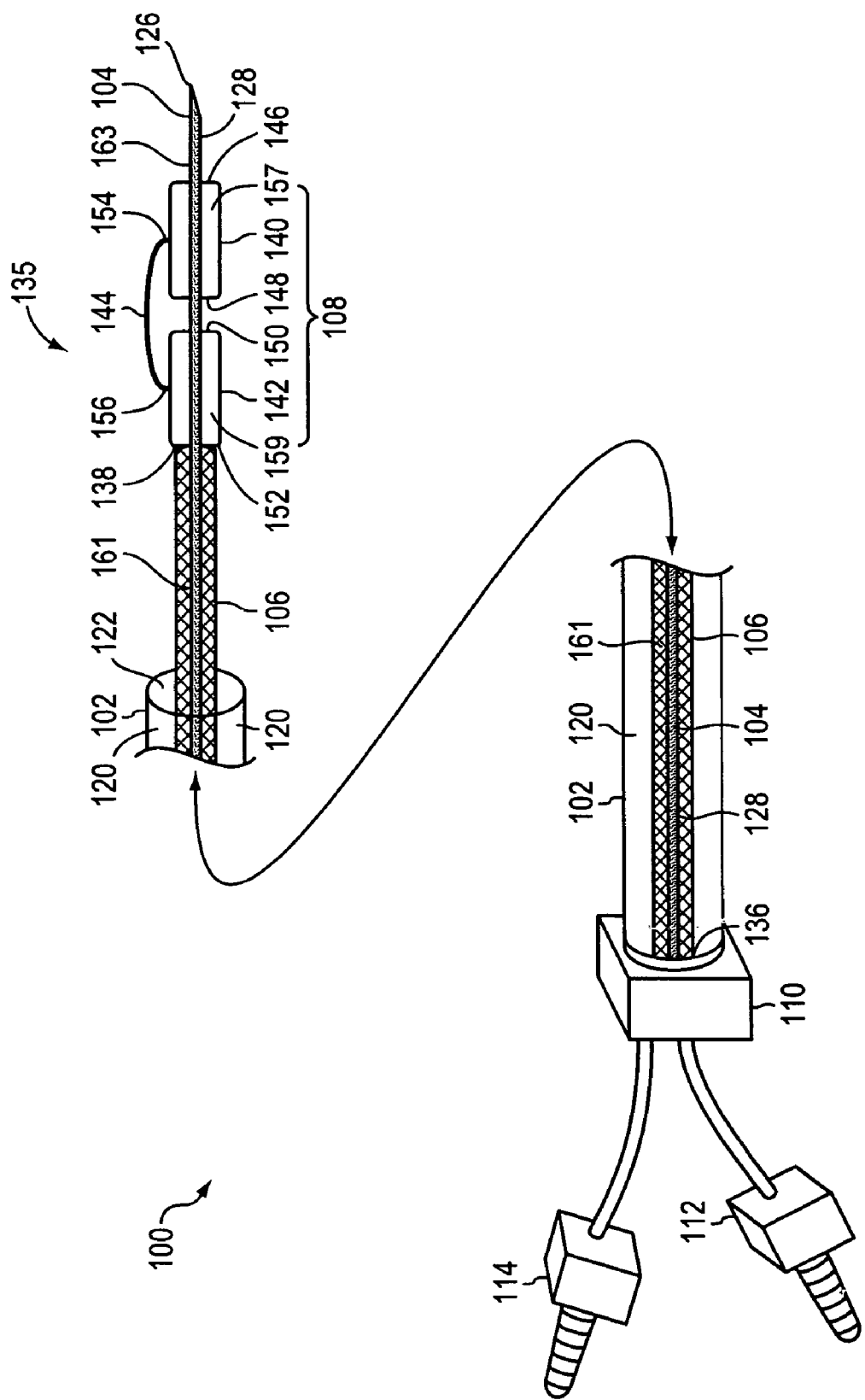
FIG. 6 is a schematic fragmented view of a tissue suturing system according to another illustrative embodiment of the invention.

FIG. 6 depicts the tissue suturing system 100 according to another illustrative embodiment of the invention. Referring now to FIGS. 5 and 6, in one embodiment, the first tissue engaging member 140 includes a lumen 157 that extends from the first end 146 to the second end 148 of the first tissue engaging member 140, and the second tissue engaging member 142 includes a lumen 159 that extends from the first end 150 to the second end 152 of the second tissue engaging member 142. Accordingly, in one embodiment, as depicted in FIG. 6, the elongate member 104 may be initially positioned within and through the lumen 159 of the second tissue engaging member 142 and within and through the lumen 157 of the first tissue engaging member 140.

With reference to FIG. 6, in one embodiment, the delivery member 106 includes a lumen 161 that extends from the proximal end 136 to the distal end 138 of the delivery member 106. Accordingly, the elongate member 104 may also be initially positioned within and through the lumen 161 of the delivery member 106. In another embodiment, the delivery member 106, the first tissue engaging member 140, and the second tissue engaging member 142 are slideably moved over an outer surface 163 of the wall 128 of the elongate member 104. Extending the delivery member 106 toward the distal end 126 of the elongate member 104 extends the suturing device 108 toward the distal end 126 of the elongate member 104 and distal to the distal end 126 of the elongate member 104. Additionally, in another embodiment, one or both ends 146, 148 of the first tissue engaging member 140 and/or one or both ends 150, 152 of the second tissue engaging member 142 are rounded, tapered, or beveled to facilitate the passage of the first tissue engaging member 140 and/or the second tissue engaging member 142 through a patient's tissues.

Referring again to FIG. 5, in one embodiment, as shown, the first fixed end 154 of the first interconnecting member 144 is connected to the first tissue engaging member 140 at a point located between the first end 146 and the second end 148 of the first tissue engaging member 140, rather than at one of the opposing ends 146, 148 of the first tissue engaging member 140. Accordingly, in such an embodiment, the first fixed end 154 of the first intereconnecting member 144 is connected to the intermediate portion 147 of the first tissue engaging member 140 and the opposing ends 146, 148 of the first tissue engaging member 140 are both free ends. Alternatively, in another embodiment, the first fixed end 154 of the first interconnecting member 144 is connected to the first tissue engaging member 140 either at the first end 146 or at the second end 148 of the first tissue engaging member 140. Accordingly, in such an embodiment, one of the first end 146 and the second end 148 of the first tissue engaging member 140 is a fixed end. In a similar fashion, the second fixed end 156 of the first interconnecting member 144 may be connected to the second tissue engaging member 142 at a point located between the first end 150 and the second end 152 of the second tissue engaging member 142 (i.e., the first interconnecting member 144 may be connected to the intermediate portion 151 of the second tissue engaging member 142), or, alternatively, at one of the opposing ends 150, 152 of the second tissue engaging member 142.

In one embodiment, the first interconnecting member 144 is connected at its first fixed end 154 to the first tissue engaging member 140 and at its second fixed end 156 to the second tissue engaging member 142 by, for example, an adhesive, such as a glue. Alternatively, the first interconnecting member 144 includes a first hinge 158 at its first fixed end 154 and a second hinge 160 at its second fixed end 156. In one such embodiment, the first hinge 158 connects the first interconnecting member 144 to the first tissue engaging member 140 and the second hinge 160 connects the first interconnecting member 144 to the second tissue engaging member 142. In one embodiment, the first hinge 158 and the second hinge 160 allow for rotational movement of the first tissue engaging member 140 and the second tissue engaging member 142, respectively, relative to each other and relative to the first interconnecting member 144.

In one embodiment, the suturing device 108 is pre-assembled (e.g., manufactured) so that the first interconnecting member 144 continuously connects the first tissue engaging member 140 to the second tissue engaging member 142. In other words, the physician need not, at any point during his or her use of the suturing system 100, connect one portion of the first interconnecting member 144 to another portion of the first interconnecting member 144, or connect either one of the two tissue engaging members 140, 142 to the first interconnecting member 144. Rather, the suturing device 108 is insertable into a patient in its connected configuration, illustrated in, and described with respect to, for example, FIG. 5.

In one embodiment, the first interconnecting member 144 is made from a flexible yet resilient material, allowing the first interconnecting member 144 to alternate between a deformed position (e.g., a bent position), as illustrated in FIGS. 2 and 6, and an unstressed position, such as the straight configuration illustrated in FIG. 5. In one embodiment, the first interconnecting member 144 alternates between the deformed and unstressed positions through the application and removal of, respectively, a force. Referring to FIG. 5, in the unstressed position of the first interconnecting member 144, a longitudinal axis of the first tissue engaging member 140 and a longitudianal axis of the second tissue engaging member 142 are, in one embodiment, each substantially perpendicular to a longitudinal axis of the first interconnecting member 144. With reference to FIGS. 2 and 6, in the deformed position of the first interconnecting member 144, a longitudinal axis of the first tissue engaging member 140 and a longitudinal axis of the second tissue engaging member 142 are, in one embodiment, each substantially parallel to the longitudinal axis of the first interconnecting member 144.

Referring to FIG. 2, in operation, in one embodiment, the suturing device 108 is initially positioned within the lumen 130 of the elongate member 104 with its first interconnecting member 144 in the deformed position. Moreover, in one embodiment, the wall 128 of the elongate member 104 constrains the first interconnecting member 144 of the suturing device 108 in the deformed position while the suturing device 108 is located within the lumen 130 of the elongate member 104. Once the suturing device 108 is advanced distally to exit through the opening 132 at the distal end 126 of the elongate member 104, the resiliency of the first interconnecting member 144 causes, in one embodiment, the first interconnecting member 144 of the suturing device 108 to regain its unstressed position, illustrated in FIG. 5.

Exemplary resilient materials from which the first interconnecting member 144 can be manufactured include bioabsorbable materials such as, but not exclusively, polylactic acid (PLA), polyethylene glycol (PEG), polycaprolactone (PCL), polyglycolic acid (PGA), or magnesium, non-resorbable materials such as, but not exclusively, a metal (e.g., nitinol) or a polymer (e.g., urethane), and/or rubber.

In some embodiments of the invention, the first interconnecting member 144 of the suturing device 108 possesses elastic properties. For example, in one embodiment, the first interconnecting member 144 can be stretched, and thereafter returned to its original state when the stretching force is removed. More particularly, in one embodiment, as the first interconnecting member 144 is stretched, moving the first tissue engaging member 140 away from the second tissue engaging member 142, a restoring force is generated in the first interconnecting member 144. The restoring force acts to pull the first tissue engaging member 140 back towards the second tissue engaging member 142 when the stretching force is removed. Exemplary elastic materials from which the first interconnecting member 144 can be manufactured include bioabsorbable materials such as, but not exclusively, polylactic acid (PLA), polyethylene glycol (PEG), polycaprolactone (PCL), or polyglycolic acid (PGA), non-resorbable materials such as, but not exclusively, a polymer or a polymer blend (e.g., urethane), and/or rubber.

Referring now to FIG. 5, in one embodiment, the first tissue engaging member 140 and/or the second tissue engaging member 142 are substantially cylindrical. Alternatively, the first tissue engaging member 140 and the second tissue engaging member 142 may have other shapes (e.g., a rectangular prism). In another embodiment, one or both of the first tissue engaging member 140 and the second tissue engaging member 142 has/have an atraumatic structure, i.e., is/are devoid of any outward projections or protrusions that might cause injury or trauma to a patient's tissue. There is, therefore, no impediment to contacting a patient's tissue directly and intimately with the first tissue engaging member 140 and/or the second tissue engaging member 142. For example, in one embodiment where the tissue engaging members 140, 142 are atraumatic, one or both of the opposing ends 146, 148 of the first tissue engaging member 140 and/or one or both of the opposing ends 150, 152 of the second tissue engaging member 142 are rounded.

In one embodiment, the first interconnecting member 144 has a length of between about 1.0 mm and about 20.0 mm and a cross-sectional diameter between about 0.01 mm and about 2.0 mm. In another embodiment, a tissue engaging member, for example the first tissue engaging member 140, has a length 162 from about 1.0 mm to about 20.0 mm and a cross-sectional diameter 164 from about 0.05 mm to about 5.0 mm.

Figure 7:
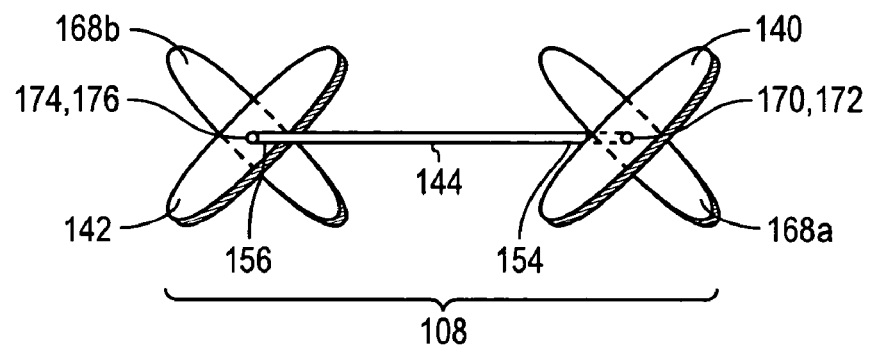
FIG. 7 is a schematic perspective view of a suturing device according to another illustrative embodiment of the invention.

FIG. 7 depicts the suturing device 108 according to another illustrative embodiment of the invention. According to the illustrative embodiment, the suturing device 108 also includes one or more third tissue engaging members 168. For example, the suturing device 108 includes two third tissue engaging members 168a, 168b, one of which is connected to the first fixed end 154 of the first interconnecting member 144 and another of which is connected to the second fixed end 156 of the first interconnecting member 144. In one embodiment, a midpoint 170 along the longitudinal axis of the first tissue engaging member 140 is connected to a midpoint 172 along the longitudinal axis of a third tissue engaging member 168a. In one embodiment, the first tissue engaging member 140 and that third tissue engaging member 168a are delivered, through the lumen 130 of the elongate member 104, co-axially. Upon exiting the opening 132 at the distal end 126 of the elongate member 104, the first tissue engaging member 140 and that third tissue engaging member 168a rotate, for example, relative to one another such that, in one embodiment, the longitudinal axis of the first tissue engaging member 140 is oriented substantially perpendicular to the longitudinal axis of that third tissue engaging member 168a, thereby forming a cross or an X-shape. Similarly, a midpoint 174 along the longitudinal axis of the second tissue engaging member 142 may be connected to a midpoint 176 along the longitudinal axis of another third tissue engaging member 168b. In one embodiment, the second tissue engaging member 142 and that third tissue engaging member 168b are delivered, through the lumen 130 of the elongate member 104, co-axially. Upon exiting the opening 132 at the distal end 126 of the elongate member 104, the second tissue engaging member 142 and that third tissue engaging member 168b rotate, for example, relative to one another such that, in one embodiment, the longitudinal axis of the second tissue engaging member 142 is oriented substantially perpendicular to the longitudinal axis of that third tissue engaging member 168b, thereby forming a cross or an X-shape. Alternatively, in other embodiments, when the suturing device 108 exits the opening 132 at the distal end 126 of the elongate member 104, the longitudinal axis of the first tissue engaging member 140 and the longitudinal axis of the second tissue engaging member 142 are each oriented at an angle between 0 degrees and 180 degrees relative to the longitudinal axis of their respective third tissue engaging member 168a, 168b.

Figure 8:
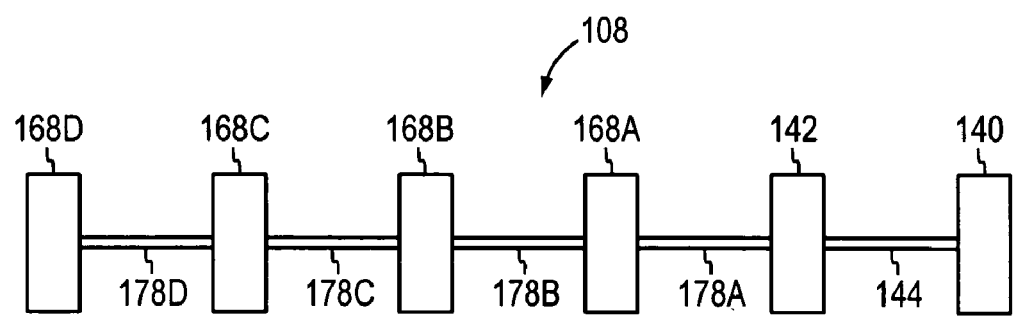
FIG. 8 is a schematic side view of a suturing device according to another illustrative embodiment of the invention.

FIG. 8 depicts the suturing device 108 according to yet another illustrative embodiment of the invention. According to the illustrative embodiment, the suturing device 108 further includes one or more second interconnecting members 178. For example, in one embodiment, the suturing device 108 includes a chain of second interconnecting members 178. In one such embodiment, at least one of the second interconnecting members 178 is connected to either the first tissue engaging member 140 or the second tissue engaging member 142. For example, as illustrated in FIG. 8, a second interconnecting member 178A is connected to the second tissue engaging member 142. Moreover, each one of the second interconnecting members 178 in the chain may be separated from an adjacent second interconnecting member 178 by a third tissue engaging member 168. For example, as illustrated in FIG. 8, a second interconnecting member 178A is separated from an adjacent second interconnecting member 178B by a third tissue engaging member 168A. Accordingly, the suturing device 108 of the invention may consist of a series of alternating tissue engaging members and interconnecting members. Any number of alternating tissue engaging members and interconnecting members may be connected in series to form the chain. Moreover, in general, the second interconnecting members 178 may include some or all of the properties of the first interconnecting member 144 described above, including, for example, the resiliency of the first interconnecting member 144. Accordingly, the second interconnecting members 178 may also alternate between a deformed position and an unstressed position.

Figure 9:
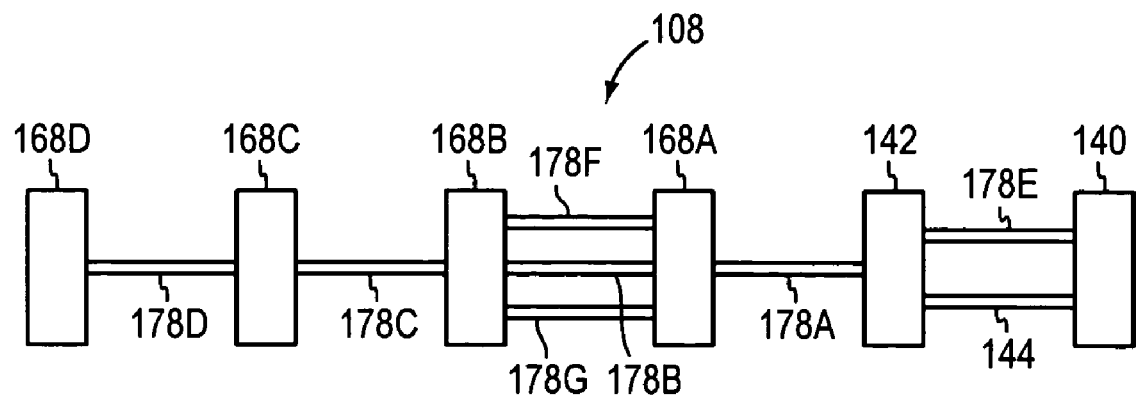
FIG. 9 is a schematic side view of a suturing device according to another illustrative embodiment of the invention.

FIG. 9 depicts the suturing device 108 according to still another illustrative embodiment of the invention. According to the illustrative embodiment, two or more interconnecting members may connect adjacent tissue engaging members. For example, both the first interconnecting member 144 and a second interconnecting member 178E may connect the first tissue engaging member 140 to the second tissue engaging member 142. Similarly, as another example, three second interconnecting members 178B, 178F, 178G may connect two adjacent third tissue engaging members 168A, 168B.

Figure 10:
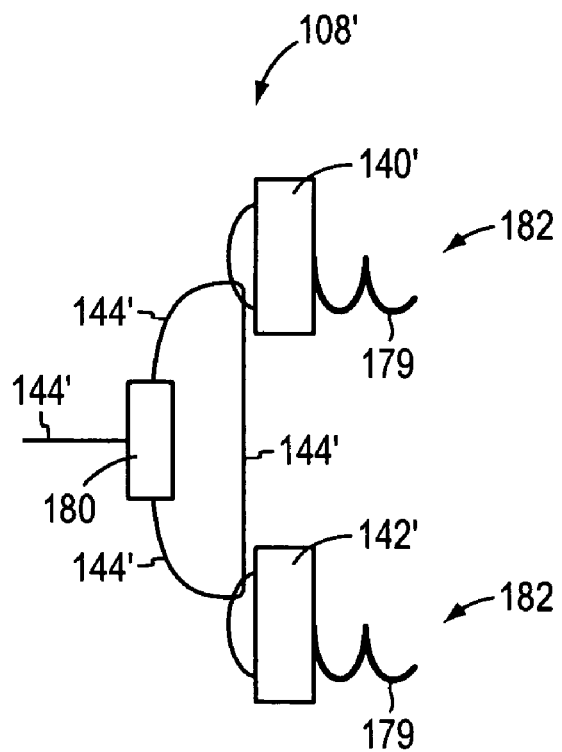
FIG. 10 is a schematic side view of a suturing device according to another illustrative embodiment of the invention.

FIG. 10 depicts a suturing device 108' according to another illustrative embodiment of the invention. The exemplary suturing device 108' includes a first interconnecting member 144', a first tissue engaging member 140', and a second tissue engaging member 142' similar to those described above. In one embodiment, the suturing device 108' additionally includes a tightening mechanism 180 connected to the first interconnecting member 144'. The first interconnecting member 144' may be, for example, a thread. Following implantation of the suturing device 108' in the patient's tissues, the tightening mechanism 180 may be used to remove a slack in the first interconnecting member 144' between the first tissue engaging member 140' and the second tissue engaging member 142'. In one embodiment, for example, the tightening mechanism 180 is a ratchet. Alternatively, in other embodiments, the tightening mechanism 180 is a wire-tie, a slip-knot, or a screw mechanism.

Figure 11:
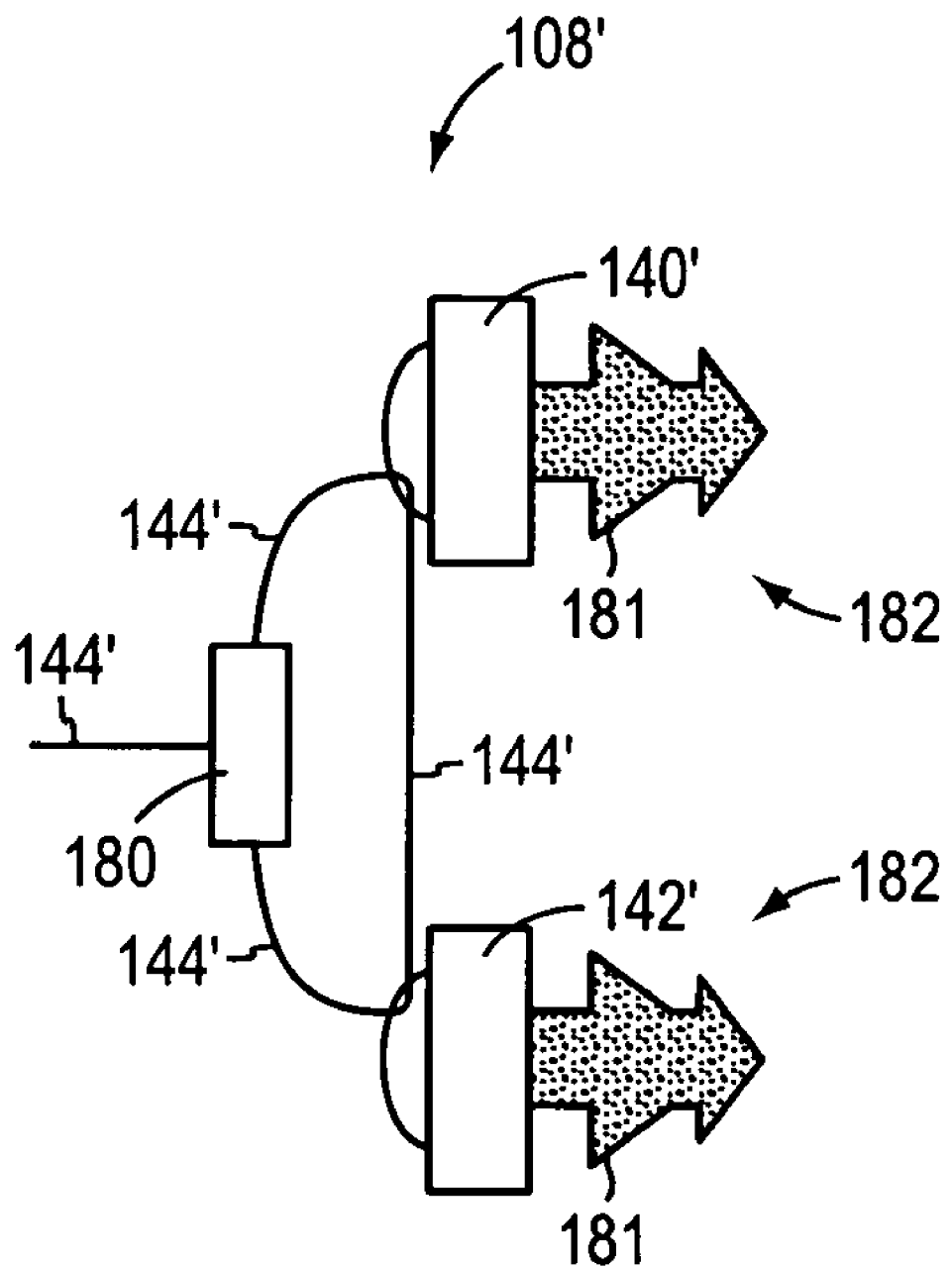
FIG. 11 is a schematic side view of a suturing device according to another illustrative embodiment of the invention.

In one embodiment, referring still to FIG. 10, the first tissue engaging member 140' and/or the second tissue engaging member 142' includes an anchor 182, such as, for example, a spiral tissue anchor 179. Accordingly, the first tissue engaging member 140' and/or the second tissue engaging member 142' may be screwed into a patient's tissues. Alternatively, in another embodiment, the first tissue engaging member 140' and/or the second tissue engaging member 142' includes a differently shaped anchor 182 for implanting the tissue engaging member 140', 142' into the patient's tissue. For example, the first tissue engaging member 140' and/or the second tissue engaging member 142' may include a barbed tissue anchor 181, as illustrated in FIG. 11. Accordingly, the barbed tissue anchor 181 of the first tissue engaging member 140' and/or the second tissue engaging member 142' may be pushed into a patient's tissues to secure the engaging member 140', 142' in the patient's tissues.

Some or all of the tissue engaging members 140, 140', 142, 142', 168, the interconnecting members 144, 144', 178, and the tightening mechanism 180 may be manufactured from a bioabsorbable material that, following placement in the patient's body, biodegrades over time and is absorbed into the patient's body, such as, for example, polylactic acid (PLA), polyethylene glycol (PEG), polycaprolactone (PCL), polyglycolic acid (PGA), or magnesium. In other embodiments, some or all of the tissue engaging members 140, 140', 142, 142', 168, the interconnecting members 144, 144', 178, and the tightening mechanism 180 may be manufactured from a biological material (e.g., an extracellular matrix material) that allows for tissue ingrowth when the suturing device 108, 108' is implanted within a patient's tissues. In yet other embodiments, some or all of the tissue engaging members 140, 140', 142, 142', 168, the interconnecting members 144, 144', 178, and the tightening mechanism 180 are coated and/or impregnated with a material (e.g., a reactive material) for stimulating tissue growth. In one embodiment, the growth stimulating material is collagen. In another embodiment, the growth stimulating material is a growth factor, such as a vascular endothelial growth factor, a basic fibro growth factor, or an angiogenic growth factor. In yet another embodiment, the growth stimulating material is a pharmacological agent for stimulating tissue growth, such as, for example, cells or genes. Alternatively, in still another embodiment, the growth stimulating material is an irritant for encouraging an inflammatory response, such as, for example, cotton seed oil or alcohol.

Materials that are not bio-absorbable could, alternatively, be used to manufacture different parts of the suturing device 108, 108'. The tissue engaging members 140, 140', 142, 142', 168 and/or the tightening mechanism 180 could, for example, be manufactured using a polymer material, (e.g., polyethylene, nylon, polypropylene, polyester, or polyurethane), a shape memory material, or a metal. For their part, the interconnecting members 144, 144', 178 could, for example, be manufactured using a polymer material, (e.g., polyethylene or polyurethane), a shape memory material, a metal, a thread, a spring, or an elastomer. For example, the tissue engaging members 140, 140', 142, 142', 168, and the interconnecting members 144, 144', 178 could be manufactured using a nickel-titanium alloy, such as Nitinol. As another example, the tissue engaging members 140, 140', 142, 142', 168, and the interconnecting members 144, 144', 178 can be manufactured as an integral unit by, for example, molding or stamping them from a single piece of material, such as a polymer.

In yet another embodiment, some or all of the tissue engaging members 140, 140', 142, 142', 168, the interconnecting members 144, 144', 178, and the tightening mechanism 180 are coated with a material that reduces thrombosis, such as, for example, heparin. In still another embodiment, some or all of the tissue engaging members 140, 140', 142, 142', 168, the interconnecting members 144, 144', 178, and the tightening mechanism 180 include a radiopaque material.

Figure 12A:
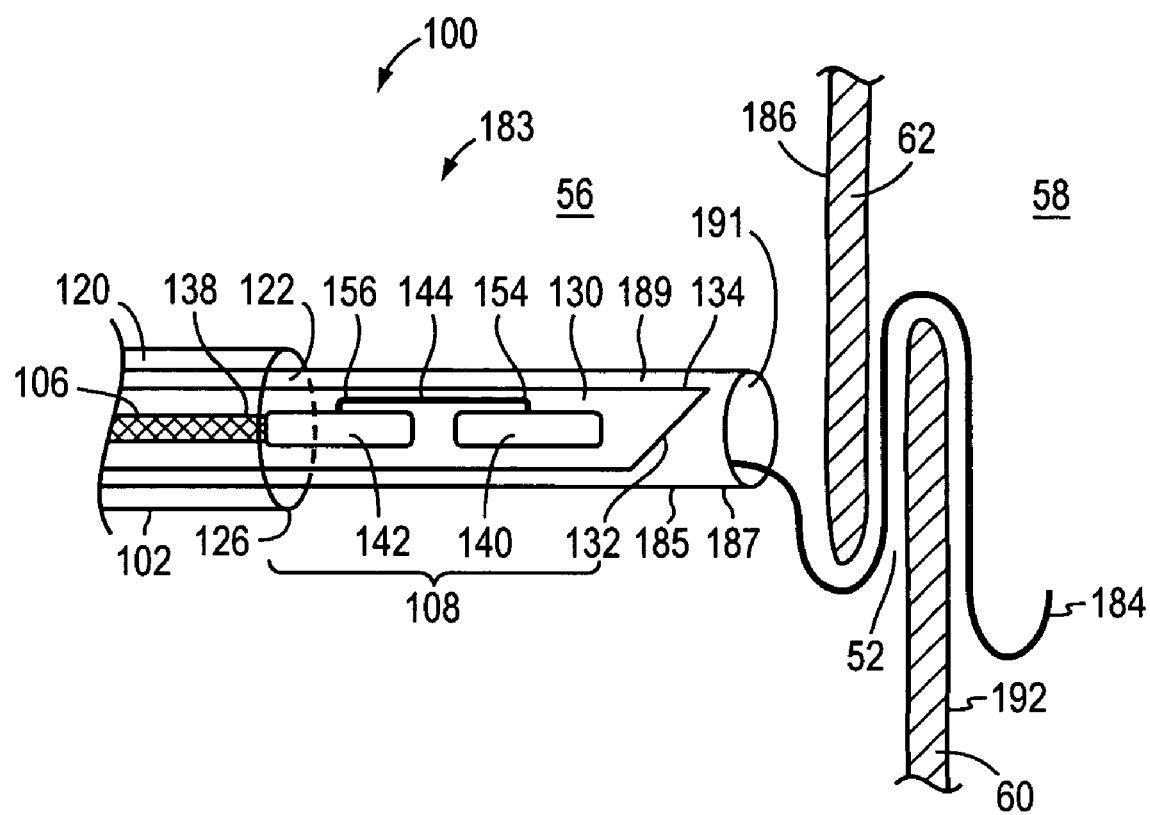
FIGS. 12A-12D illustrate the stages in one embodiment of a method for suturing the intraatrial septum in the heart of a patient in accordance with the invention.

In another aspect, the invention provides a method for suturing tissue. FIGS. 12A-12D illustrate one embodiment of a method for percutaneously suturing closed a patent foramen ovale 52 in the intraatrial septum in the heart of a patient in accordance with the invention. Referring first to FIG. 12A, the physician positions a distal end 183 of a tissue suturing system, such as the tissue suturing system 100 of FIG. 2, within the right atrium 56 of the patient in proximity to the septum secundum 62.

Optionally, as illustrated in FIG. 12A, the physician also employs a tissue stabilization device 184 with the tissue suturing system 100. In one such embodiment, the tissue stabilization device 184 is connected to a catheter 185. The catheter 185 includes a proximal end (not shown), a distal end 187, a lumen 189 that extends from the proximal end to the distal end 187, and an opening 191 that is positioned at the distal end 187 of the catheter 185 and that is in fluid communication with the lumen 189 of the catheter 185. In one embodiment, as illustrated, the catheter 185 is positioned within the lumen 120 of the sheath 102. The elongate member 104, the delivery member 106, and the suturing device 108 are positioned within the lumen 189 of the catheter 185.

In one embodiment, the physician positions the tissue stabilization device 184 within and through the patent foramen ovale 52 between the septum secundum 62 and the septum primum 60 of the patient's heart. The tissue stabilization device 184 is used by the physician to, for example, limit movement of the septum secundum 62 and the septum primum 60 prior to forming, as explained below, holes through the septum secundum 62 and the septum primum 60 with the cutting member 134 of the elongate member 104. The tissue stabilization device 184 also serves to position the distal end 187 of the catheter 185 in the area where the septum secundum 62 and the septum primum 60 overlap. Accordingly, when the elongate member 104 is extended to exit through the opening 191 at the distal end 187 of the catheter 185, the cutting member 134 of the elongate member 104 pierces holes through the septum secundum 62 and the septum primum 60 in the area where they overlap. In accordance with the method further described below, the suturing device 108 is thereby placed through the septa 60, 62 in the area where they overlap.

Exemplary tissue stabilization devices and flexible members suitable for stabilizing cardiac tissues in a patient and for placing the elements described above in the area where the septum secundum 62 and the septum primum 60 overlap include those described in U.S. patent application Ser. No. 10/660,444, the disclosure of which is hereby incorporated herein by reference in its entirety. For example, the tissue stabilization device 184 may: i) be a flexible coil having a spiral shape, illustrated in FIG. 12A, ii) include three flexible hexagonal members forming, generally, a planar array, iii) include two flexible members, each one of which includes a leg, such as a wire, that is pre-shaped to articulate one or more times upon exit from a lumen, iv) include two flexible members, each one of which includes a loop section, or v) be a single flexible member that forms a closed loop.

Alternatively, in another embodiment, the physician does not employ the tissue stabilization device 184 in suturing the patent foramen ovale 52. Accordingly, while FIGS. 12B-12D do not, for the purposes of simplifying and clarifying the drawings, illustrate the tissue stabilization device 184, it is understood that the tissue stabilization device may or may not be present in practice.

Figure 12B:
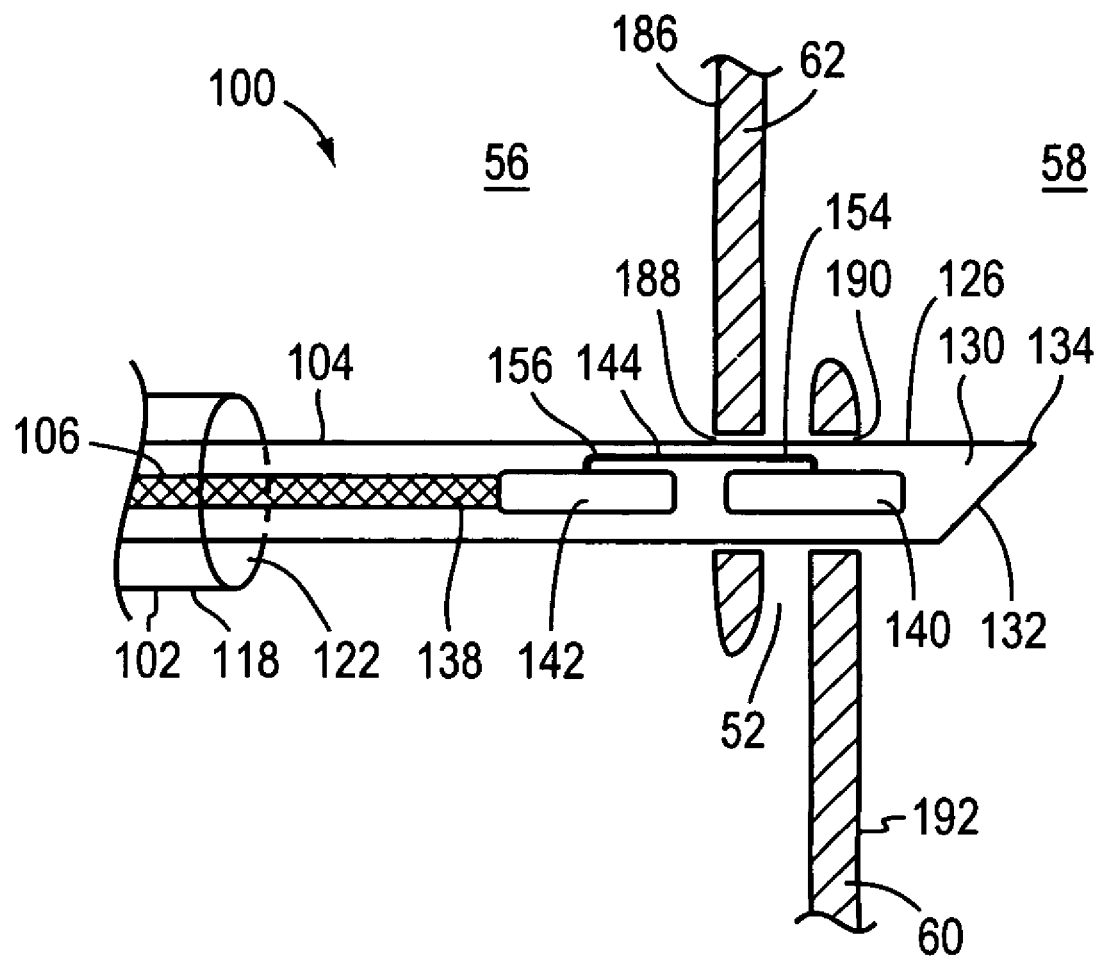

Referring now to FIG. 12B, the physician extends, in one embodiment, the elongate member 104 distally, so that the cutting member 134 of the elongate member 104 contacts a tissue surface 186 of the septum secundum 62 at a point where the septum secundum 62 overlaps the septum primum 60. By continuing to advance the elongate member 104, the physician forms a first hole 188 in the septum secundum 62 and, subsequently, a second hole 190 in the overlapping septum primum 60.

Figure 12C:
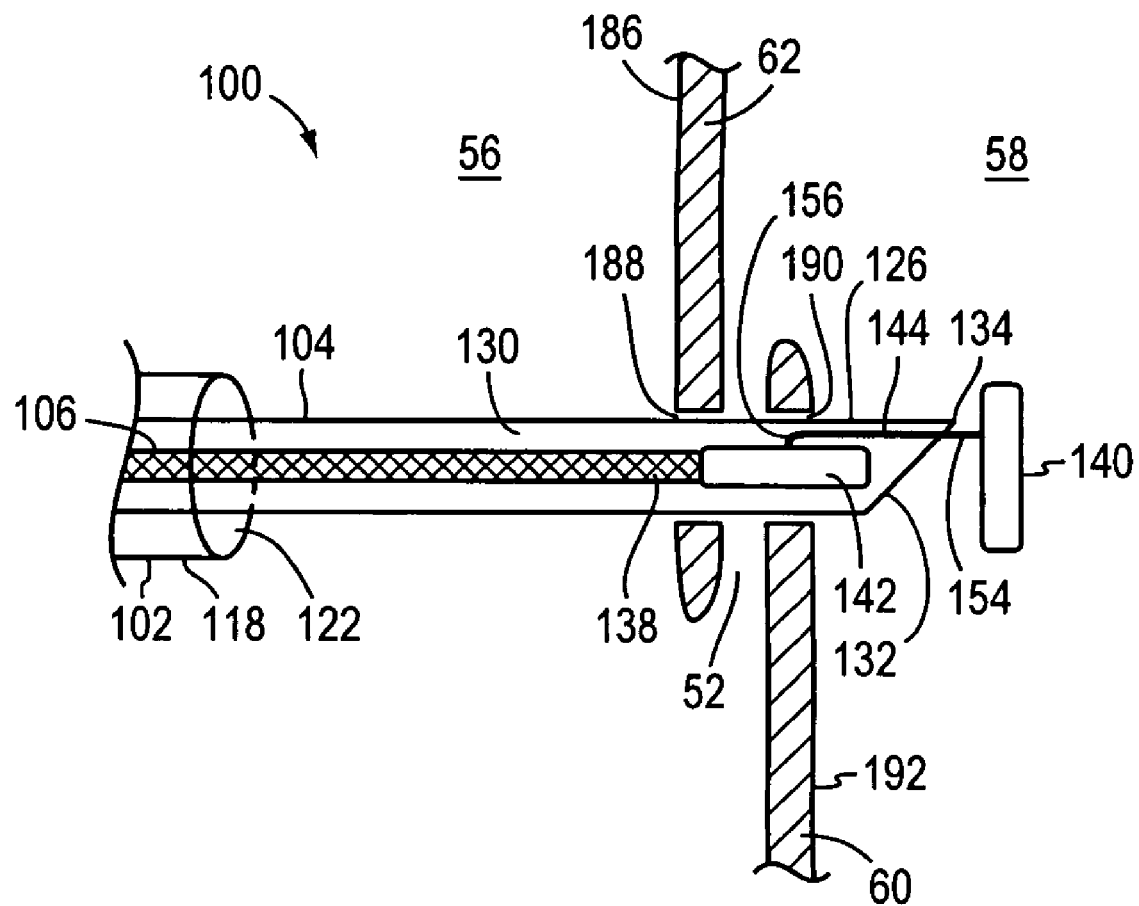

Referring now to FIG. 12C, with the distal end 126 of the elongate member 104 in the left atrium 58, the delivery member 106 is advanced toward the distal end 126 of the elongate member 104 until the first tissue engaging member 140 exits the opening 132 at the distal end 126 of the elongate member 104. Once the first tissue engaging member 140 exits the opening 132, the resiliency of the first interconnecting member 144 causes the first fixed end 154 of the first interconnecting member 144 to return to an unstressed (e.g., a straight) position, such that the longitudinal axis of the first tissue engaging member 140 is substantially perpendicular to the longitudinal axis of the first interconnecting member 144.

Figure 12D:
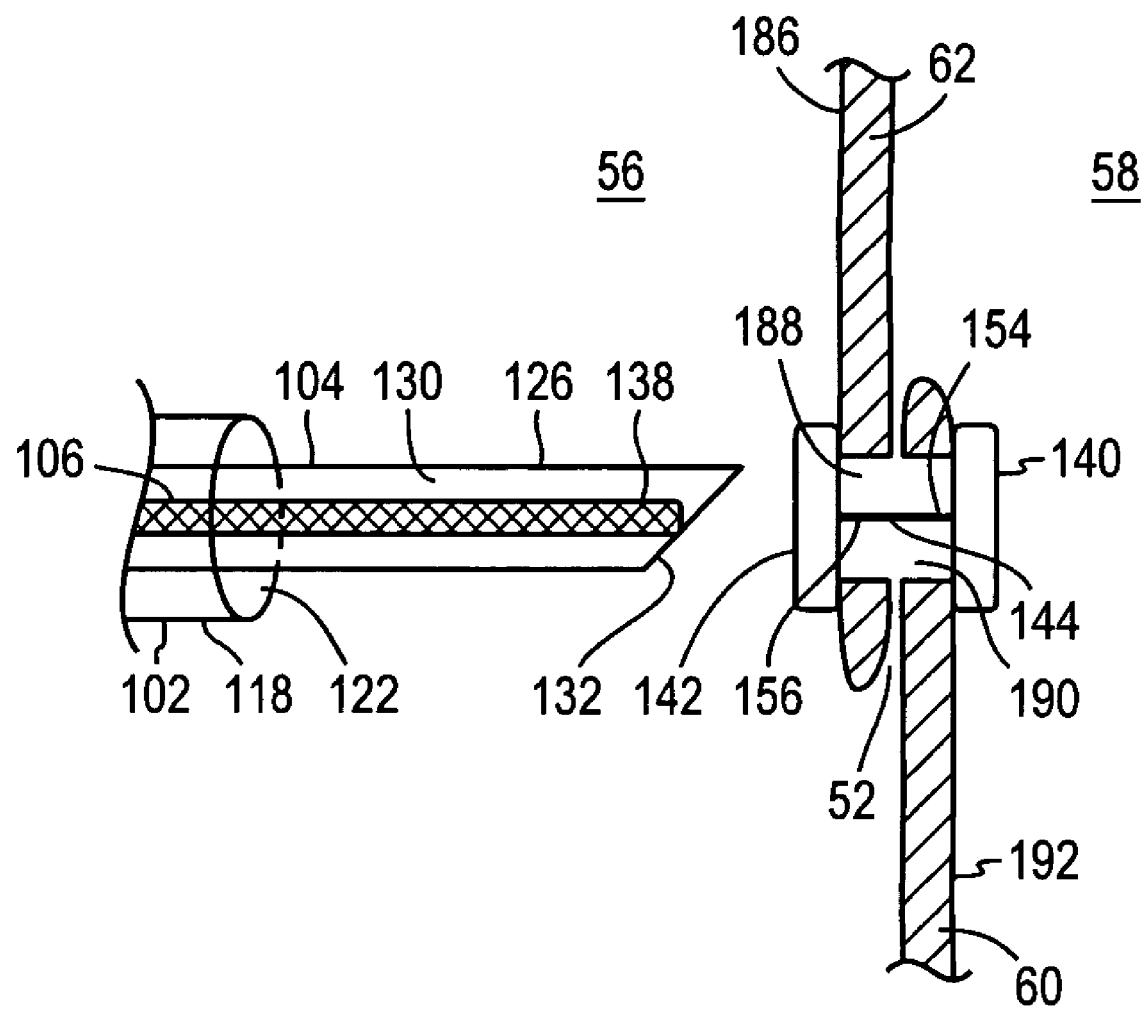

Referring now to FIG. 12D, the physician then retracts the elongate member 104 proximally back through the second hole 190 and the first hole 188, such that the first tissue engaging member 140 is located adjacent a surface 192 of the septum primum 60. The physician continues to retract the elongate member 104 until the distal end 126 of the elongate member 104 is positioned in the right atrium 56. The delivery member 106 is then further advanced distally until the second tissue engaging member 142 exits the opening 132 at the distal end 126 of the elongate member 104. Once the second tissue engaging member 142 exits the opening 132, the resiliency of the first interconnecting member 144 causes the second fixed end 156 of the first interconnecting member 144 to return to an unstressed (e.g., a straight) position, such that the longitudinal axis of the second tissue engaging member 142 is substantially perpendicular to the longitudinal axis of the first interconnecting member 144. The second tissue engaging member 142 is thereby positioned adjacent a tissue surface 186 of the septum secundum 62. Configured as such, the suturing device 108 holds the septum primum 60 and the septum secundum 62 between the first tissue engaging member 140 and the second tissue engaging member 142.

Figure 13:
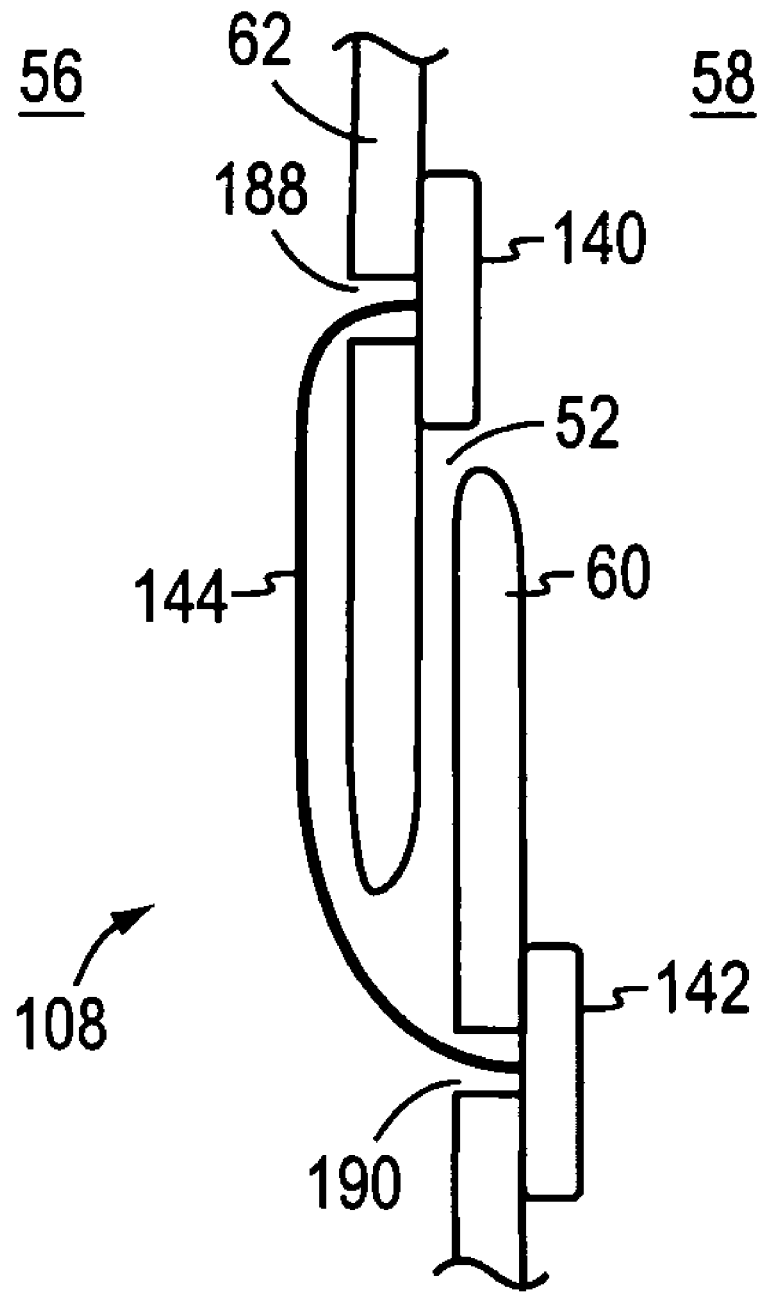
FIG. 13 illustrates a suturing device implanted into the intraatrial septum in the heart of a patient in accordance with another embodiment of the invention.

FIG. 13 depicts a suturing device 108 implanted into the intraatrial septum in the heart of a patient in accordance with another embodiment of the invention. According to the illustrative embodiment, rather than creating the first hole 188 through the septum secundum 62 and the second hole 190 through the septum primum 60 at a point where the septum secundum 62 and the septum primum 60 overlap, as described above, the physician creates the holes 188, 190 at a point where the septum secundum 62 and the septum primum 60 do not overlap. For example, the physician uses the cutting member 134 to create the first hole 188 through the septum secundum 62, positions the first tissue engaging member 140 in the left atrium 58 adjacent a tissue surface of the septum secundum 62, proximally withdraws the elongate member 104 back into the right atrium 56, uses the cutting member 134 to create the second hole 190 through the septum primum 60, positions the second tissue engaging member 142 in the left atrium 58 adjacent a tissue surface of the septum primum 60, and proximally withdraws the elongate member 104 back into the right atrium 56 for eventual removal from the patient's body. The suturing device 108 thus captures the septum primum 60 and the septum secundum 62 as illustrated in FIG. 13, without occupying a position in the tunnel of the patent foramen ovale 52. Alternatively, in another embodiment, the physician creates the holes 188, 190 in the septum secundum 62 and the septum primum 60 in the opposite order.

Figure 14:
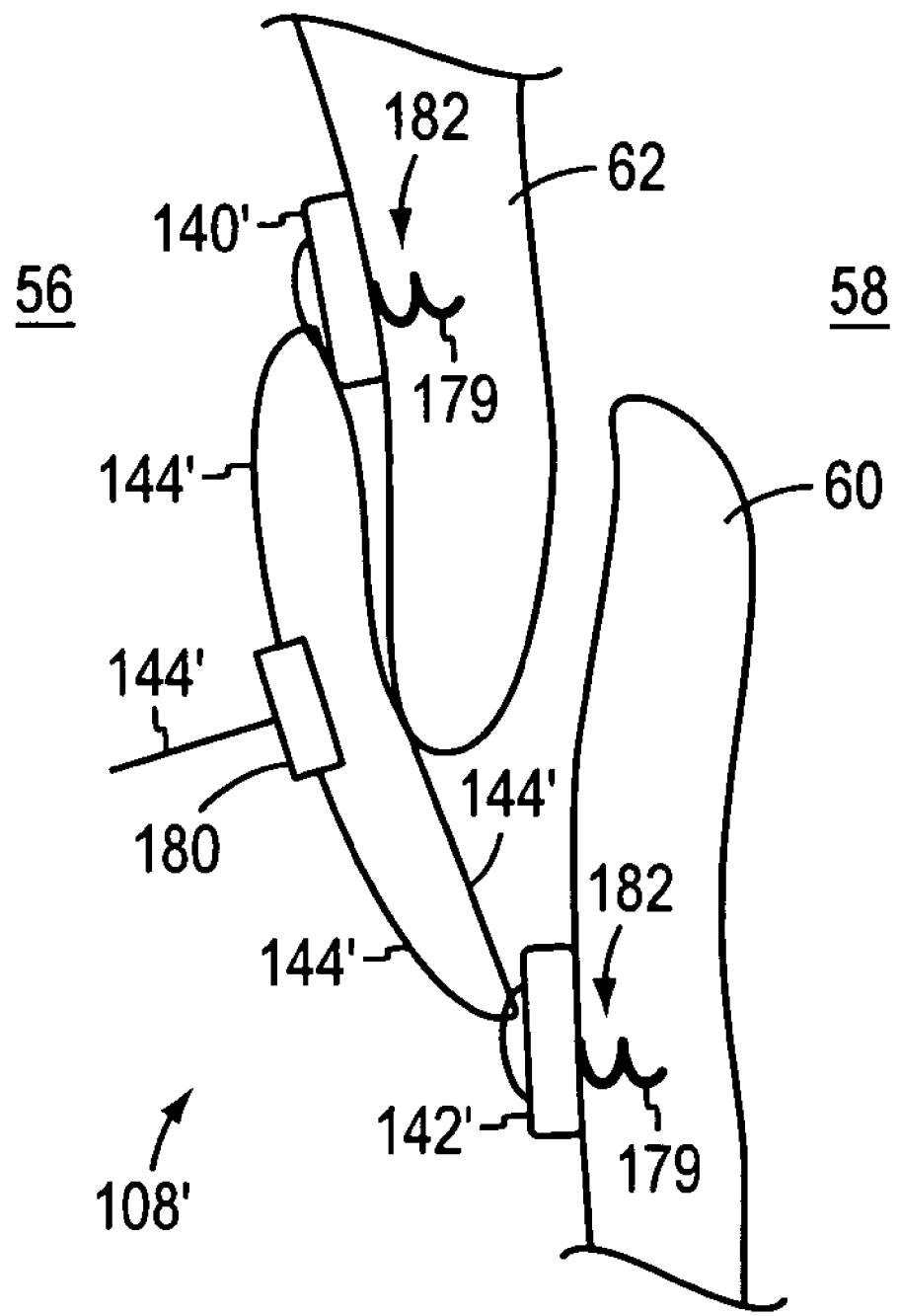
FIG. 14 illustrates a suturing device implanted into the intraatrial septum in the heart of a patient in accordance with another embodiment of the invention.

FIG. 14 depicts a suturing device 108' implanted into the intraatrial septum in the heart of a patient in accordance with another embodiment of the invention. According to the illustrative embodiment, rather than forming holes 188, 190 through the septum secundum 62 and the septum primum 60 to access the left atrium 58, the physician advances the spiral tissue anchors 179 (or the barbed tissue anchors 181) of the tissue engaging members 140', 142' into the right atrial wall of the septum primum 60 and the septum secundum 62. In one such embodiment, the distal end 126 of the elongate member 104 is adapted to engage the tissue engaging members 140', 142' as they are advanced by the delivery member 106 to the distal end 126 of the elongate member 104. Once a tissue engaging member 140', 142' is engaged by the distal end 126 of the elongate member 104, the physician then rotates the elongate member 104 to screw the spiral tissue anchor 179 of the tissue engaging member 140', 142' into the patient's tissue, or, alternatively, the physician advances the elongate member 104 to push the barbed tissue anchor 181 of the tissue engaging member 140', 142' into the patient's tissue. Accordingly, the suturing device 108' captures the septum primum 60 and the septum secundum 62 as illustrated in FIG. 14. Optionally, the physician may then use the tightening mechanism 180 to remove any slack in the first interconnecting member 144' between the first tissue engaging member 140' and the second tissue engaging member 142'.

In other embodiments, to deliver a suturing device 108, 108' that includes a series of alternating tissue engaging members and interconnecting members, as illustrated in FIGS. 8 and 9, the physician repeats the steps described above with reference to either FIGS. 12A-12D, FIG. 13, or FIG. 14. In some such embodiments, to distally advance the suturing device 108, 108' through the lumen 130 of the elongate member 104, the delivery member 106 abuts the distal most tissue engaging member (e.g., the third tissue engaging member 168D in FIGS. 8 and 9) in the series of alternating tissue engaging members and interconnecting members.

It should be understood that the order of the steps in the above described methods and/or the order for performing certain actions is immaterial so long as the invention remains operable. Moreover, two or more steps or actions may be conducted simultaneously.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for suturing partially overlapping tissue flaps in a mammalian heart, comprising:
    loading a suturing device into an elongate member to form a suturing system, said elongate member comprising a cutting member and said suturing device comprising
        a first tissue engaging member
        a second tissue engaging member, and
        a first interconnecting member comprising a first fixed end connected to the first tissue engaging member, and a second fixed end connected to the second tissue engaging member thereby connecting the first tissue engaging member to the second tissue engaging member;
    inserting the suturing system into a right atrium of the heart
    puncturing a first through-hole in a first tissue flap at a non-overlapping portion of the flaps with the cutting member of the elongate member;
    introducing the first tissue engaging member of the suturing device through the first through-hole and into the left atrium while connected to the second tissue engagement member;
    positioning the first tissue engaging member on a surface of the tissue flap substantially approximal to the first through-hole;
    retracting the elongate member proximally from the left atrium into the right atrium in the heart;
    puncturing a second through-hole in a second tissue-flap with the cutting member of the elongate member before retracting the elongate member from the heart;
    introducing the second tissue engaging member of the suturing device while connected to the first tissue engaging member through the second through-hole and into the left atrium; and
    positioning the second tissue engaging member on a surface of the tissue flap substantially approximal to the second through-hole; and
    retracting the elongate member from the heart.

2. The method for suturing tissue of claim 1, the suturing system further comprising a tissue stabilization device and the method further comprising positioning the tissue stabilization device in a patent foramen ovale.

3. The method of claim 1, wherein the second through-hole is positioned at a non-overlapping portion of the flaps.

4. The method of claim 1, wherein the first interconnecting member of the suturing device is substantially located in the right atrium of the heart.

5. The method of claim 1, wherein the tissue flaps comprise a septum primum and a septum secundum of an intraatrial septum of the heart.

6. A method for suturing partially overlapping tissue flaps in a mammalian heart, comprising:
    loading a suturing device into an elongate member to form a suturing system, said suturing device comprising:
        a first tissue engaging member;

a second tissue engaging member; and a first interconnecting member connecting the first tissue engaging member to the second tissue engaging member;

inserting the suturing system into a right atrium of the heart;

securing the first tissue engaging member to a first tissue flap at a non-overlapping portion of the flaps;

withdrawing the elongate member proximally into the right atrium;

securing the second tissue engaging member to a second tissue flap at a second non-overlapping portion of the flaps; and retracting the elongate member from the heart.

7. The method for suturing tissue of claim 6, wherein the suturing device further comprises a first anchor connected to the first tissue engaging member and a second anchor connected to the second tissue engaging member.

8. The method of claim 7, wherein at least one of the first anchor and the second anchor is a spiral tissue anchor.

9. The method for suturing tissue of claim 8, wherein at least one of the steps of securing the first tissue engaging member or the second tissue engaging member further comprises rotating the spiral tissue anchor into the tissue surface.

10. The method of claim 7, wherein at least one of the first anchor and the second anchor is a barbed tissue anchor.

11. The method for suturing tissue of claim 10, wherein at least one of the steps of securing the first tissue engaging member or the second tissue engaging member further comprises pushing the barbed tissue anchor into the tissue surface.

12. The method of claim 6, wherein the suturing device further comprises a tightening mechanism for removing a slack in the first interconnecting member between the first tissue engaging member and the second tissue engaging member.

13. The method of claim 12, further comprising the step of tightening the first interconnecting member to close an opening between the tissue flaps.

14. The method of claim 6, wherein the suturing system further comprises a tissue stabilization device and the method further comprises positioning the tissue stabilization device in a patent foramen ovale.

15. The method of claim 6, wherein the tissue flaps comprise a septum primum and a septum secundum of an intraatrial septum in the heart.

* * * * *